United States Patent
Hirai et al.

(10) Patent No.: US 7,421,105 B2
(45) Date of Patent: Sep. 2, 2008

(54) METHOD FOR STAINING CORNEOCYTES, METHOD FOR PREPARING CORNEOCYTES SPECIMEN AND SKIN ANALYSIS SYSTEM

(75) Inventors: Yoshikazu Hirai, Yokohama (JP); Kenya Hirayama, Yokohama (JP); Nobuo Kashibuchi, Yokohama (JP); Sonoko Kawasaki, Yokohama (JP); Hiroaki Imai, Yokohama (JP); Yoko Zemba, Yokohama (JP); Takanori Takahashi, Yokohama (JP); Seiichi Takaya, Tokyo (JP); Chikako Kamata, Tokyo (JP); Toshikazu Yagi, Fukuroi (JP); Jiro Yabusaki, Shizuoka (JP)

(73) Assignee: Pola Chemical Industries Inc., Shizuoka (JP)

( * ) Notice: Subject to any disclaimer, the term of this patent is extended or adjusted under 35 U.S.C. 154(b) by 848 days.

(21) Appl. No.: 10/848,233

(22) Filed: May 18, 2004

(65) Prior Publication Data

US 2004/0214336 A1  Oct. 28, 2004

Related U.S. Application Data

(62) Division of application No. 10/123,440, filed on Apr. 15, 2002, now abandoned.

(30) Foreign Application Priority Data

| Oct. 29, 2001 | (JP) | ............ 2001-331072 |
| Oct. 29, 2001 | (JP) | ............ 2001-331073 |
| Mar. 6, 2002 | (JP) | ............ 2002-60346 |
| Mar. 6, 2002 | (JP) | ............ 2002-60347 |

(51) Int. Cl.
*G06K 9/00* (2006.01)
*G01N 1/30* (2006.01)
*G01N 33/48* (2006.01)
*C12N 5/08* (2006.01)

(52) U.S. Cl. ............ 382/133; 435/40.5; 435/371
(58) Field of Classification Search ............ 382/133, 382/128; 435/40.5, 371
See application file for complete search history.

(56) References Cited

U.S. PATENT DOCUMENTS 3,678,151 A * 7/1972 Horonick et al. ............ 435/40.5

(Continued)

FOREIGN PATENT DOCUMENTS

EP  0 750 884 A1  1/1997

(Continued)

OTHER PUBLICATIONS

Schatz, Harald et al, quantification of dry (xerotic) skin by image analysis of scales romvoed by adhesive discs (D-Squames), Jun. 28, 1992, J. Joc. Cosmet. Chem, Jan./Feb. 1993, all pages.*

(Continued)

*Primary Examiner*—Bhavesh Mehta
*Assistant Examiner*—Kathleen S Yuan
(74) *Attorney, Agent, or Firm*—Knobbe, Martens, Olson & Bear, LLP

(57) ABSTRACT

A method for preparing corneocites specimen, which comprises stripping off corneocites from the surface of a skin using an adhesive material, staining the corneocites in a solution of stain in solvent containing a water-miscible organic solvent, and mounting the stained corneocites into an oil and fat constituent and/or composition that is liquid at 1 atm, 25° C.

7 Claims, 22 Drawing Sheets

U.S. PATENT DOCUMENTS

| | | | |
|---|---|---|---|
| 4,831,242 A * | 5/1989 | Englehardt et al. | 235/382 |
| 5,141,874 A | 8/1992 | Saint-Leger et al. | |
| 5,202,130 A | 4/1993 | Grant et al. | |
| 5,202,931 A | 4/1993 | Bacus | |
| 5,298,258 A * | 3/1994 | Akemi et al. | 424/484 |
| 5,650,165 A | 7/1997 | Akemi et al. | |
| 5,667,789 A | 9/1997 | Collin et al. | |
| 5,683,710 A | 11/1997 | Akemi et al. | |
| 6,026,174 A | 2/2000 | Palcic et al. | |
| 6,275,777 B1 | 8/2001 | Shimizu | |
| 7,024,045 B2 * | 4/2006 | McIntyre | 382/239 |

FOREIGN PATENT DOCUMENTS

| | | |
|---|---|---|
| JP | 63-113358 | 5/1988 |
| JP | 09-131323 | 5/1997 |
| JP | 10-243935 | 9/1998 |
| JP | 11-016450 | 1/1999 |
| JP | H11-299792 | 11/1999 |
| JP | 2000-005134 | 1/2000 |
| JP | 2000-125854 | 5/2000 |
| JP | 2000-212036 | 8/2000 |
| JP | 2001-78968 | 3/2001 |
| SU | 1352366 A1 | 11/1987 |
| WO | WO 01/04828 | 1/2001 |
| WO | WO 01/31566 | 5/2001 |
| WO | WO 01/72215 | 10/2001 |

OTHER PUBLICATIONS

Machine translation of Japanese Application Publication H11-299792, Kashibuchi et al, all pages.*

"H&E Mount" http://www.innvx.com/innovexmountingmediatech.html.*

Luna, Lee, Routine Mayer's Hematoxylin and Eosin Stain (H&E), 1960, McGraw Hill Publishers, Manual of Histologic Staining methods of the Armed Forces Institute of Pathology (third edition).*

Johannesson, et al. "The Rate of Corneocyte Formation in Microscopic Lesions in Patients with Active Psoriasis," *British Journal of Dermatology*, vol. 105, pp. 391-404, 1981.

Corcuff, et al. "Quantitative Aspect of Corneocytes," *Journal of Society of Cosmetic Chemists*, vol. 33, No. 1, pp. 1-8, 1982.

International Search Report, completed Jul. 22, 2003, issued in a related application.

Abstract, Database WPI, Section Ch, Week 198824, Derwent Publications Ltd., London, GB, p. 002, AN 1988-166617, EX-002229997 & SU 1 352 366 A (Tselinograd Medicin), Nov. 15, 1987.

Schatz, et al. "Quantification of Dry (Xerotic) Skin by Image Analysis of Scales Removed by Adhesive Discs (D-Squames)," *Journal of the Society of Cosmetic Chemists*, vol. 44, pp. 53-63, Jan./Feb. 1993.

* cited by examiner

FIG. 7 cof

POL cosmetic future
skin-care advise system

CUSTOMER'S NAME | ○○○○
CUSTOMER'S ID | 01-002550
DATE OF TEST | 2002.01.13

ENTRY (REFERENCE) SPACE

1. TOTAL SKIN SCORE
2. GENERAL CHART
3. SKIN POSITIONING
4. ROUGHNESS OF THE SURFACE OF KERATINIZED LAYER
5. COMPLETENESS OF KERATINIZED LAYER
6. TEXTURE
7. DARK SPOT/COLOR EVENNESS
8. SENSITIVE SKIN TYPE
9. SKINCARE ADVICE
   - LOTION
   - MOISTURE ESSENCE
   - CLEANSING
   - WASH
   - SPECIAL ITEM
10. TRIAL KIT
11. SKIN BIORHYTHM
12. UTILITY

FIG. 10 skin-care advise system

| | | |
|---|---|---|
| 1. TOTAL SKIN SCORE | | |
| 2. GENERAL CHART | | |
| 3. SKIN POSITIONING | | |
| 4. ROUGHNESS OF THE SURFACE OF KERATINIZED LAYER | ☀ | ABILITY TO KEEP MOISTURE |
| 5. COMPLETENESS OF KERATINIZED LAYER | ☁ | OILINESS (SEBUM) |
| 6. TEXTURE | ☀ | TENDENCY TO ACNE |
| 7. DARK SPOT/COLOR EVENNESS | ☂☀ | DARK SPOT/COLOR EVENNESS |
| 8. SENSITIVE SKIN TYPE | | WRINKLE/TEXTURE |
| 9. SKINCARE ADVICE | ☁ | SENSITIVITY |
|    LOTION | | |
|    MOISTURE ESSENCE | | |
|    CLEANSING | | |
|    WASH | | |
|    SPECIAL ITEM | | |
| 10. TRIAL KIT | | |
| 11. SKIN BIORHYTHM | | |
| 12. UTILITY | | |

BAD ← AVERAGE FOR THE SAME GENERATION → GOOD

[COMPARISON WITH 4288 PANELISTS OF AGES 24–26]

[YOUR TENDENCY] [COMPARISON WITH THE SAME GENERATION]

MARKED WITH SYMBOLS FOR EASY RECOGNITION

SWITCH ICON (HIGHLIGHTED WHEN ACTIVE)

- GRAPH SHOWING COMPARISON WITH THE SAME GENERATION
  1. ABILITY TO KEEP MOISTURE
  2. OILINESS (SEBUM)
  3. TENDENCY TO ACNE
  4. DARK SPOT/COLOR EVENNESS
  5. WRINKLE/TEXTURE
  6. SENSITIVITY
  (6 AXES, A 10-POINT SCALE FOR EACH AXIS)
- COMPARISON WITH THE SAME GENERATION
  CENTRAL AXIS INDICATES THE AVERAGE FOR THE SAME GENERATION AND THE CUSTOMER'S DATA ARE SHOWN IN RELATION TO THE AXIS

FIG. 20

*skin-care advise system*

| | |
|---|---|
| 1. TOTAL SKIN SCORE | |
| 2. GENERAL CHART | |
| 3. SKIN POSITIONING | MOISTURE COAT — MOISTURE COAT (FOR NORMAL/OILY SKIN) / DESCRIPTION OF CHARACTERISTIC + VOLUME, PRICE |
| 4. ROUGHNESS OF THE SURFACE OF KERATINIZED LAYER | |
| 5. COMPLETENESS OF KERATINIZED LAYER | SPOTS — WHITENING / PHARMACEUTICAL WHITENING SPOTS / DESCRIPTION OF CHARACTERISTIC + VOLUME, PRICE |
| 6. TEXTURE | |
| 7. DARK SPOT/COLOR EVENNESS | |
| 8. SENSITIVE SKIN TYPE | PACK — CLAY PACK / DESCRIPTION OF CHARACTERISTIC + VOLUME, PRICE |
| 9. SKINCARE ADVICE | |
|    LOTION | |
|    MOISTURE ESSENCE | |
|    CLEANSING | |
|    WASH | |
|    SPECIAL ITEM | ADDITIONAL ITEM — FACE SUNSCREEN / DESCRIPTION OF CHARACTERISTIC + VOLUME, PRICE |
| 10. TRIAL KIT | |
| 11. SKIN BIORHYTHM | |
| 12. UTILITY | |

ITEM NAME DISPLAYED / CORRESPONDING PRODUCT NAME DISPLAYED

* ITEM NAME
* INFORMATION ON CORRESPONDING PRODUCT DISPLAYED (DESCRIPTION OF CHARACTERISTICS AND OTHER INFORMATION FOR EACH PRODUCT)

FIG. 21

*skin-care advise system*

MS. OOOO
RECOMMENDED TRIAL KIT FOR YOU CONTAINS:

LOTION

WATER FORMULA N55   ooooo
                    ooo-ooooo
DESCRIPTION OF CHARACTERISTIC
+ VOLUME

MOISTURE ESSENCE

ESSENCE FORMULA W55   ooooo
                      ooo-ooooo
                      WHITENING
DESCRIPTION OF CHARACTERISTIC
+ VOLUME

WASH

WASHING CREAM (FOR NORMAL/OILY SKIN
DESCRIPTION OF CHARACTERISTIC
+ VOLUME

DESCRIPTION OF PRODUCT
* ITEM NAME
* DESCRIPTION OF CHARACTERISTICS AND OTHER INFORMATION FOR EACH PRODUCT

1. TOTAL SKIN SCORE
2. GENERAL CHART
3. SKIN POSITIONING
4. ROUGHNESS OF THE SURFACE OF KERATINIZED LAYER
5. COMPLETENESS OF KERATINIZED LAYER
6. TEXTURE
7. DARK SPOT/COLOR EVENNESS
8. SENSITIVE SKIN TYPE
9. SKINCARE ADVICE
   LOTION
   MOISTURE ESSENCE
   CLEANSING
   WASH
   SPECIAL ITEM
10. TRIAL KIT
11. SKIN BIORHYTHM
12. UTILITY

FIG. 22

*skin-care advise system*

MS. ○○○○
YOUR SKIN BIORHYTHM GRAPH IS SHOWN BELOW:

SPRING  SUMMER  AUTUMN  WINTER
MS. ○○○○ ——— AVERAGE FOR THE SAME GENERATION
          —·— COMPARISON WITH THE SAME GENERATION (AGES 24-26)

| | | |
|---|---|---|
| SENSITIVITY | TOTAL SKIN SCORE | |
| WRINKLE/TEXTURE | | OILINESS |
| TENDENCY TO ACNE | | ABILITY TO KEEP MOISTURE |

1. TOTAL SKIN SCORE
2. GENERAL CHART
3. SKIN POSITIONING
4. ROUGHNESS OF THE SURFACE OF KERATINIZED LAYER
5. COMPLETENESS OF KERATINIZED LAYER
6. TEXTURE
7. DARK SPOT/COLOR EVENNESS
8. SENSITIVE SKIN TYPE
9. SKINCARE ADVICE
   LOTION
   MOISTURE ESSENCE
   CLEANSING
   WASH
   SPECIAL ITEM
10. TRIAL KIT
11. SKIN BIORHYTHM
12. UTILITY

*CHECK ITEMS AND CORRESPONDING CHECK BOXES
*TIME-COURSE GRAPH OF THE RESULTS

CHECK BOXES

METHOD FOR STAINING CORNEOCYTES, METHOD FOR PREPARING CORNEOCYTES SPECIMEN AND SKIN ANALYSIS SYSTEM

This application is a divisional of U.S. application Ser. No. 10/123,440, filed Apr. 15, 2002 now abandoned which claims priority to Japanese Patent Application No. 2002-60347, filed on Mar. 6, 2002, Japanese Patent Application No. 2002-60346, filed on Mar. 6, 2002, Japanese Patent Application No. 2001-331073, filed on Oct. 29, 2001, and Japanese Patent Application No. 2001-331072, filed on Oct. 29, 2001.

BACKGROUND OF THE INVENTION

The present invention relates to a method for staining corneocites as well as a method for preparing corneocites specimen which can provide useful information for analysis of skin condition and appropriate selection of cosmetic products.

The present invention also relates to a skin analysis system which can provide useful information for analysis of skin condition and appropriate selection of cosmetic products.

Skin conditions may constantly change depending on variable factors including seasonal changes, physical conditions, skin treatment (e.g., application of cosmetic products) or the like. It is thus very important to select an appropriate cosmetic product according to such variable factors in order to prevent aging or keep skin in a good condition. For this purpose, methods for objectively and scientifically analyze skin type and/or condition have been developed. One example of such method involves collecting corneocites from, for example, the surface of face using an adhesive tape or disc, staining the corneocites, and analysis skin type and condition using as indicators various factors such as the arrangement regularity of the corneocites, a shape or size of a horny cell (corneocite), a roughness of the surface of horny stratum (keratinized layer), and the presence or absence of a nucleus in the horny cell. In such analysis, a staining method using gentian violet and brilliant green has been used since it can preferably provide a high contrast between cytoplasm and its background and thus confirm both the shape of individual corneocites and the presence or absence of a nucleus in each horny cell. This method, however, requires a relatively longer period of time for the staining step and thus cannot immediately provide data for instant analysis (e.g., a personal consultation in store). Therefore, conventional methods for selecting cosmetic products based on the analysis of skin using as an indicator the shape of horny cell took several days until it could provide cosmetic samples after skin analysis, which disadvantageously produced a time lag. Although the amount of dye can be increased in such a case, it may yet take ten minutes or more for both gentian violet and brilliant green to stain cells even when their maximal water-solubility limits (gentian violet=1%, brilliant green=0.5%) are used. Therefore, conventional method still had a disadvantage in terms of staining time. Conventionally, organic solvents have not been used in such staining process since they may reduce staining-specificity or cause degeneration or alteration of cells. Accordingly, a method for staining a horny cell has not been known yet in which a sample containing corneocites obtained by stripping off from a skin using an adhesive material (e.g., a stripper) is stained wherein a stain solution used in the staining step comprises a water-miscible organic solvent.

Generally, a stained horny cell sample may be mounted to obtain uniform refractive index through the entire sample. Balsam and ultraviolet-curing resins have conventionally been used for mountion. However, those mounting materials are not preferable since they may often cause color running, which may result in a significant error in automatic computation of, for example, the size of cell by binarization (by using a binary image of the corneocites). Moreover, an adhesive tape cannot be used to obtain corneocites since the adhesive or tape component thereof may be decomposed by the organic solvent used for mountion. For quick analysis of corneocites in, for example, a personal consultation at a customer desk as described above, automatic computation of the size of horny cell by using the binary image of the horny cell is inevitable and thus a solution to such regarding color running problem has strongly been demanded. Oil and fat constituent and/or composition that is liquid at 1 atm, 25° C. has not been used for such mountion. This is because that it is difficult to preserve such a liquid mounting agent for 1 month or more and that such constituents or compositions have never been used for mountion so far. Accordingly, it is a novel finding that, by using such mounting agents, a corneocites sample can be prepared which allows for an automatic calculation of the size of a horny cell by using the binary image of the corneocites with little or no color running.

Skin conditions may constantly change depending on variable factors including seasonal changes, physical conditions, skin treatment (e.g., application of cosmetic products) or the like. It is thus very important to select an appropriate cosmetic product according to such variable factors in order to prevent aging or keep skin in a good condition. For this purpose, methods for objectively and scientifically analyze skin type and/or condition have been developed.

In order to select cosmetic products suitable for a particular customer, for example, conventional methods involved collecting corneocites from, for example, the surface of face using an adhesive tape or disc with adhesive material, staining the corneocites, and analysis skin type and condition using as indicators various factors such as the size of horny cell, the roughness of the surface of horny stratum (keratinized layer) and the presence or absence of a nucleus in the horny cell.

In such analysis, a staining method using gentian violet and brilliant green has been used since it can preferably provide a high contrast between cytoplasm and its background and thus confirm both the shape of individual corneocites and the presence or absence of a nucleus in each horny cell.

This method, however, requires a relatively longer period of time for the staining step and thus cannot immediately provide data for instant analysis (e.g., a personal consultation in store). Therefore, conventional methods for selecting cosmetic products based on the analysis of skin using as an indicator the shape of horny cell took several days until it could provide cosmetic samples after skin analysis, which disadvantageously produced a time lag.

Therefore, no sales method has been introduced which can complete, within a day (or rather instantly), the whole process comprising analysis the skin of a customer at a store counter and recommending the customer a suitable trial cosmetic kit based on the analysis results so that the customer can purchase and try the kit and then select and purchase a full-size cosmetic product or products of the same version contained in the trial kit if he/she likes it or them.

SUMMARY OF THE INVENTION

One object of the present invention is to provide a method for staining corneocites, which can stain corneocites quickly and clearly as well as a method for preparing a corneocites specimen which can immediately provide useful data for consultation.

Another object of the present invention is to provide a skin analysis system, which can stain the corneocites quickly and clearly and provide useful data for consultation.

For these purposes, the present inventors worked hard to develop a method for staining corneocites, which can stain the corneocites quickly and clearly as well as a method for preparing a corneocites specimen which can immediately provide useful data for consultation. And they finally found that the corneocites can be stained quickly and clearly by a method for preparing a sample containing corneocites which have been striped off from the surface of the skin of the subject using an adhesive material and stained in a solution of stain in solvent containing a water-miscible organic solvent. They also found that color running can be reduced or eliminated by mounting the stained sample in an oil and fat constituent and/or composition that is liquid at 1 atm, 25° C. to prepare a horny cell specimen. This may allow for binarization of horny cell image (producing a monochromic image of the corneocites) and thus enable an automatic computation of the size of the horny cell in the corneocites specimen. Based on these findings, the present inventors developed the present invention.

In summary, the present invention relates to the following techniques:

(1) a method for staining a sample containing corneocites which have been stripped off from a surface of a skin of a subject using an adhesive material wherein the sample may be stained in a solution of stain in solvent containing a water-miscible organic solvent;

(2) a method according to (1) wherein the dye comprises gentian violet or brilliant green;

(3) a method according to (1) or (2) wherein the water-miscible organic solvent comprises ethanol;

(4) a method according to any one of (1)-(3) wherein the adhesive material comprises an adhesive tape;

(5) a method for preparing a specimen comprising a stained sample containing corneocites which have been stripped off from a surface of a skin of a subject using an adhesive material wherein the stained specimen is mounted in an oil and fat constituent and/or composition that is liquid at 1 atm, 25° C.;

(6) a method according to (5) wherein the oil and fat constituent and/or composition that is liquid at 1 atm, 25° C. is one or more selected from the group consisting of silicone oil, fatty acid triglyceride, ester of higher alcohol and fatty acid, and carbohydrate;

(7) a method according to (5) or (6) wherein the sample containing corneocites is stained according to any one of staining methods (1)-(4);

(8) a method according to any one of (5)-(7) which may be used to determine or measure one or more selected from a group consisting of a size of a horny cell, presence or absence of nuclear cell, the frequency of nuclear cell appearance, the arrangement regularity or shape of horny cell and the roughness of the surface of keratinized layer.

The present invention also relates to a skin analysis system which comprises:

a staining apparatus for staining a sample containing corneocites which haven been stripped off from the surface of the subject's skin using an adhesive material and stained in a solution of stain in solvent containing a water-miscible organic solvent;

a microscope for obtaining an enlarged image of a corneocites specimen prepared from the sample stained in the staining apparatus;

a corneocites image data generating portion for generating corneocites image data that is an image data of the enlarged image of the corneocites specimen obtained by the microscope;

a measurement portion for measuring a size of a horny cell using the enlarged image of the corneocites specimen;

a transmitting portion for transmitting to a server via a network transmits the corneocites image data and information representing the horny cell size obtained by the measurement portion;

a receiving portion for receiving from the server via the network evaluation information representing results obtained by evaluating at least one of a roughness of a surface of a keratinized layer and a completeness of the keratinized layer based on the corneocites image and the horny cell size information; and a display control portion which displays the evaluation information on a display portion.

According to the skin analysis system according to the present invention, it takes a shorter period of time to stain corneocites when compared to conventional systems. The inventive system can therefore reduce the time required until receiving, from a server, results (analysis results) obtained by evaluating at least one of the roughness of the surface of the keratinized layer and the completeness of the keratinized layer which will then be used in a personal consultation or the like.

The skin analysis system according to the present invention may be preferably designed so that a microscope may provide an enlarged image of a corneocites specimen which comprises a stained sample mounted in an oil and fat constituent and/or composition that is liquid at 1 atm, 25° C. In this way, color-running may be reduced or eliminated, and an enlarged image of corneocites can be thus obtained which can be suitably used to analyze the roughness of the surface of the keratinized layer and the completeness of the keratinized layer.

The skin analysis system according to the present invention may be preferably designed to further comprise a texture image data generating portion for generating texture image data that is a image data of an enlarged image of a surface of the subject's skin obtained by an image pickup device, wherein:

the transmitting portion may transmit the texture image data to the server;

the receiving portion may receive from the server the evaluation information including evaluation results about a condition of the texture based on the texture image; and the display control portion may display the evaluation information on a display portion.

The skin analysis system according to the present invention may be preferably designed to further comprise a dark spot image generating portion which generates B channel image data obtained by extracting B channel alone from an enlarged color image of the surface of the subject's skin obtained by an image pickup device which can be used to analyze any dark spot on the subject's skin, wherein:

the transmitting portion may transmit the B channel image data to the server;

the receiving portion may receive from the server the evaluation information including evaluation results obtained by evaluating any dark spot based on the B channel image data; and the display control portion may display the evaluation information on a display portion.

Use of B channel image can eliminate the staining step for staining the corneocites sample that was conventionally performed for dark spot analysis, which may in turn reduce the time required until the results of the evaluation obtained by dark spot analysis transmitted from the server is displayed on a display portion.

The skin analysis system according to the present invention may preferably be designed so that the display control portion may display analysis results of the subject's skin obtained on the basis of the evaluation information and analysis results obtained about persons of the same generation of the subject on a display portion so that the former can be compared with the latter. By this configuration, it may be possible to provide the subject with more useful information than a system without displaying such reference data.

The skin analysis system according to the present invention may preferably be designed so that the display control portion may display analysis results of the subject's skin obtained on the basis of the evaluation information and analysis results obtained about persons of the same generation having an age equal to the subject's age or 1 or 2 years older and younger than the subject's age on a display portion so that the former can be compared with the latter.

Further, the display control portion may preferably be designed to display the results obtained by skin analysis of the subject relative to analysis results obtained about the persons of the same generation of the subject. Preferably, the reference data may represent results obtained during the same month as the date of current skin analysis. In this way, reference data which has taken into account skin condition variable according to seasonal changes can be provided.

The present invention also provides a display data generating apparatus for skin analysis, which comprises:

a receiving portion which receives via a network data to be used in skin analysis of a subject;

a data generating portion which generates, when evaluation results of the skin analysis of the subject are obtained on the basis of the skin analysis data, a display data in order to display the evaluation results in such a form that the evaluation results can be compared with evaluation results about persons of the same generation having an age equal to the subject's age or 1 or 2 years older and younger than the subject's age; and a display transmitting portion which transmits via the network the display data to an apparatus having a display device for reproducing an image or video based on the display data.

The display data generating apparatus according to the present invention for displaying results of skin analysis may preferably be designed such that the data generating portion may generate a display data to be used to display evaluation results of the skin analysis of the subject relative to the evaluation results of the persons of the same generation.

BRIEF DESCRIPTION OF THE DRAWINGS

FIG. 7 shows an exemplary display displayed on a top (title) web page of an advice site;

FIG. 10 shows a second example of a screen representation displayed on a web page titled "2. general chart";

FIG. 20 shows an example of a screen representation displayed on a web page which presents "special items";

FIG. 21 shows an example of a screen representation displayed on a web page titled "10. trial kit";

FIG. 22 shows an example of a screen representation displayed on a web page titled "11. skin biorhythm";

DETAIL DESCRIPTION OF THE INVENTION

Figure 1:
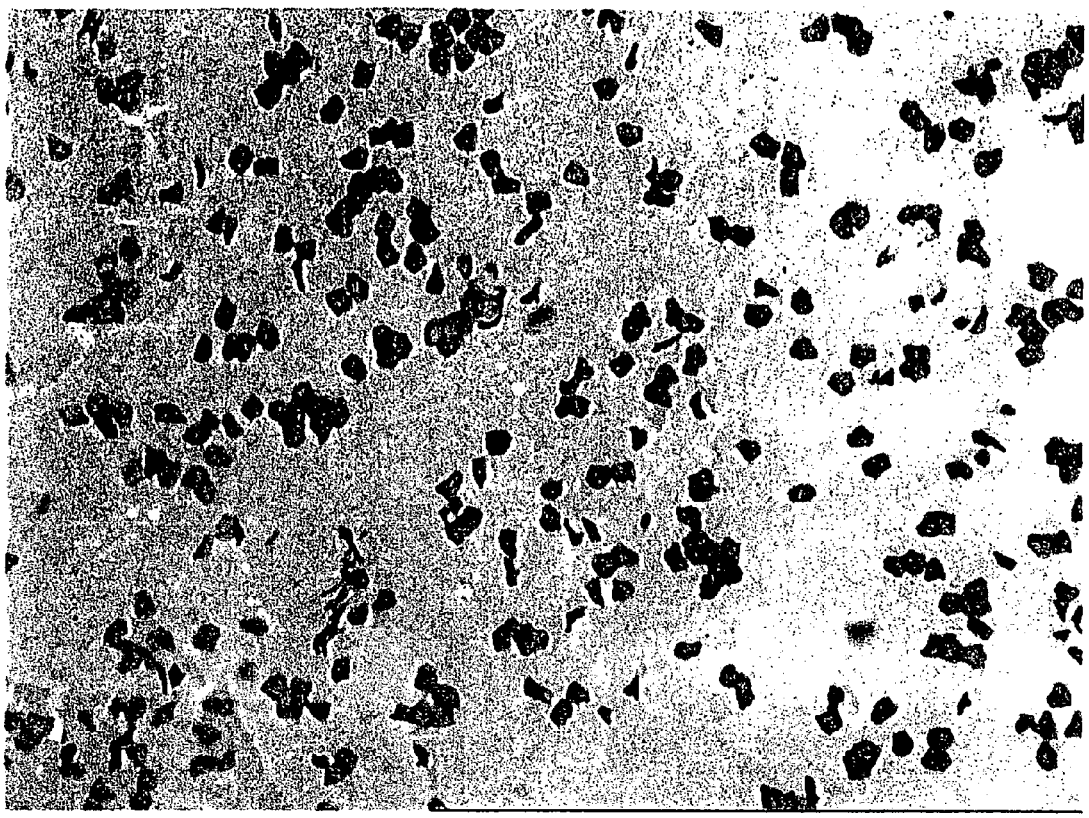
FIG. 1 shows a microscopic photograph of a horny cell specimen prepared by the method according to Example 1 of the present invention.

Hereinafter, the present invention will be described in more detail,

[1] Method for Staining Horny Cell According to the Present Invention

A method for staining horny cell according to the present invention is characterized by that a sample containing corneocites which have been stripped off from a skin using an adhesive material is stained with a solution of stain in solvent containing a water-miscible organic solvent. Examples of adhesive material preferably include adhesive transparent tapes such as cellophane-tape and adhesive discs such as those comprising a polyethylene terephthalate plate coated with an adhesive. Among all, adhesive tapes are particularly preferable since those can be commercially obtained very easily. A horny cell sample obtained by stripping corneocites off from the surface of skin using such an adhesive material may be stained directly or transferred to another adhesive material for use. Preferably, the sample obtained may be stained directly so that the time required for the process can be reduced. According to the inventive staining method, samples collected can be directly stained without affecting the adhesive or the substrate of the adhesive material (e.g., an adhesive tape or disc) used. Any conventionally-used dye can be used in the inventive staining method, preferably including eosin, hematoxylin, gentian violet, brilliant green and malachite green, which can be used alone or in combination. Among all, a combination of gentian violet and brilliant green may be particularly preferable. This is because that cytoplasm can be stained with gentian violet to obtain a high contrast between the cytoplasm and the background thereby clearly visualizing the shape of corneocites, and that the stained cytoplasm may in turn act as the background so that nuclei of the corneocites can be clearly stained with brilliant green. The inventive staining method is characterized by that a sample is stained in a solution of stain in liquid solvent containing a water-soluble organic solvent. Stain may preferably be present in the dyeing solution at an amount of 2-7% by weight. For a combination of gentian violet and brilliant green, gentian violet may preferably be present at an amount of 1.5-5% by weight and more preferably 2-4% by weight while brilliant green may preferably be present at an amount of 0.7-2% by weight and more preferably at 0.8-1.5% by weight. Examples of water-soluble organic solvent preferably include: alcohol such as methanol, ethanol, isopropanol or 1,3-butanediol; keton such as acetone or methyl ethyl ketone; nitrile such as acetinitrile; and ether such as tetrahydrofuran. Among all, alcohol is preferable and ethanol is particularly preferable. Water-soluble organic solvent may preferably be present in the liquid solvent at an amount of 3-55% by weight and more preferably 5-50% by weight. This is because that a larger amount of organic solvent may not contribute to reduction in the time required for staining or rather may degrade the adhesive or substrate of adhesive material while a smaller amount cannot stain a sample clearly. Under those conditions, it may take 1-5 minutes to stain a sample, which is much shorter than the time required for staining according to conventional methods (10-30 minutes) (using 0.5-1% by weight of gentian violet and 0.2-0.5% by weight of brilliant green). Further, a very high contrast can be obtained. Besides, the staining method using those conditions can be performed at room temperature.

[2] Method for Preparing Horny Cell Specimen According to the Present Invention

The method for preparing horny cell specimen according to the present invention is a method for preparing a specimen comprising a stained sample containing corneocites which have been stripped off from the surface of skin using an adhesive material, characterized by that the stained sample is then mounted in an oil and fat component and/or composition that is liquid at 1 atm, 25° C. Examples of stained sample containing corneocites which have been stripped off from the surface of skin using an adhesive material generally include any stained samples which have been prepared as described above. Particularly preferable are those obtained by the method for staining horny cell according to the present invention described in (1) above. Oil and fat constituent and/or composition that is liquid at 1 atm, 25° C. to be used in the inventive staining method may include oil and fat constituents which are conventionally used in cosmetic products and drugs as well as compositions comprising any combination thereof which are liquid at 1 atm, 25° C. Preferable examples may include one or any combination of two or more selected from the group consisting of silicone oil, fatty acid triglyceride, ester of higher alcohol and fatty acid, and carbohydrate which are liquid at 1 atm, 25° C. Generally, mountion in a liquid component may not provide a stability of 1 month or longer. However, this may not be critical for an instant consultation at a store counter, which is the purpose of the invention. Such oil base may not cause color running and thus a microscopic image of a specimen obtained can be processed into a binary image (binarization) based on whether the corneocites have been stained or not to provide an accurate shape (contour) of horny cell. Then, the size of horny cell can automatically be computed accurately. Additional information which can be obtained from a specimen prepared by the method for preparing specimen according to the present invention include the presence or absence of nuclear cell, the frequency of nuclear cell appearance, the roughness of the surface of keratinized layer, the arrangement regularity of corneocites, the shape of horny cell and the like. Specimen according to the present invention can preferably be used to determine numerical values for those parameters. In summary, horny cell specimens prepared by the inventive method may preferably be used to determine one or more selected from the group consisting of the size of horny cell, the presence or absence of nuclear cell, the frequency of nuclear cell appearance, the arrangement regularity of corneocites, the shape of horny cell and the roughness of the surface of keratinized layer.

EXAMPLES

The present invention will hereinafter be described in more detail in reference to Examples though it should be noted that the present invention might not be limited to these examples.

Example 1

Figure 2:
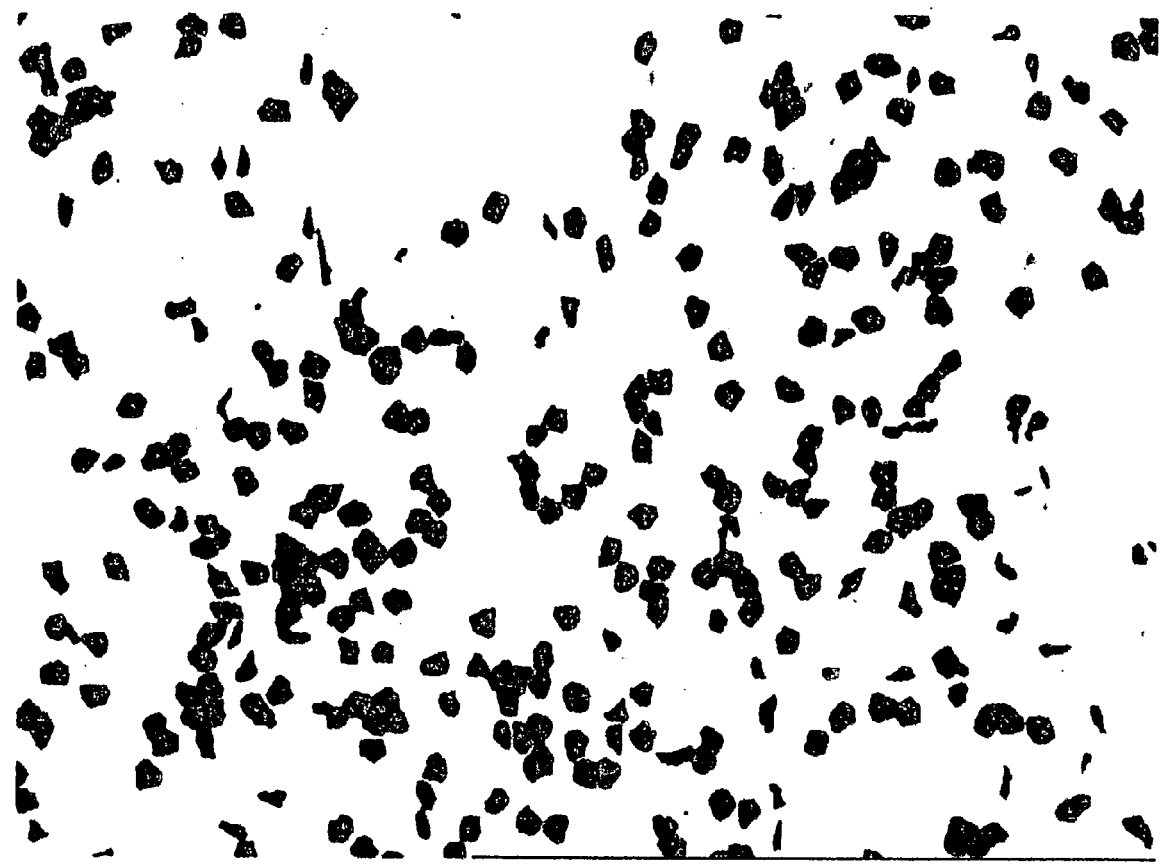
FIG. 2 shows a microscopic photograph of horny cell specimen prepared by the method according to Comparative Example 1 described in Example 1 of the present invention.
Figure 3:
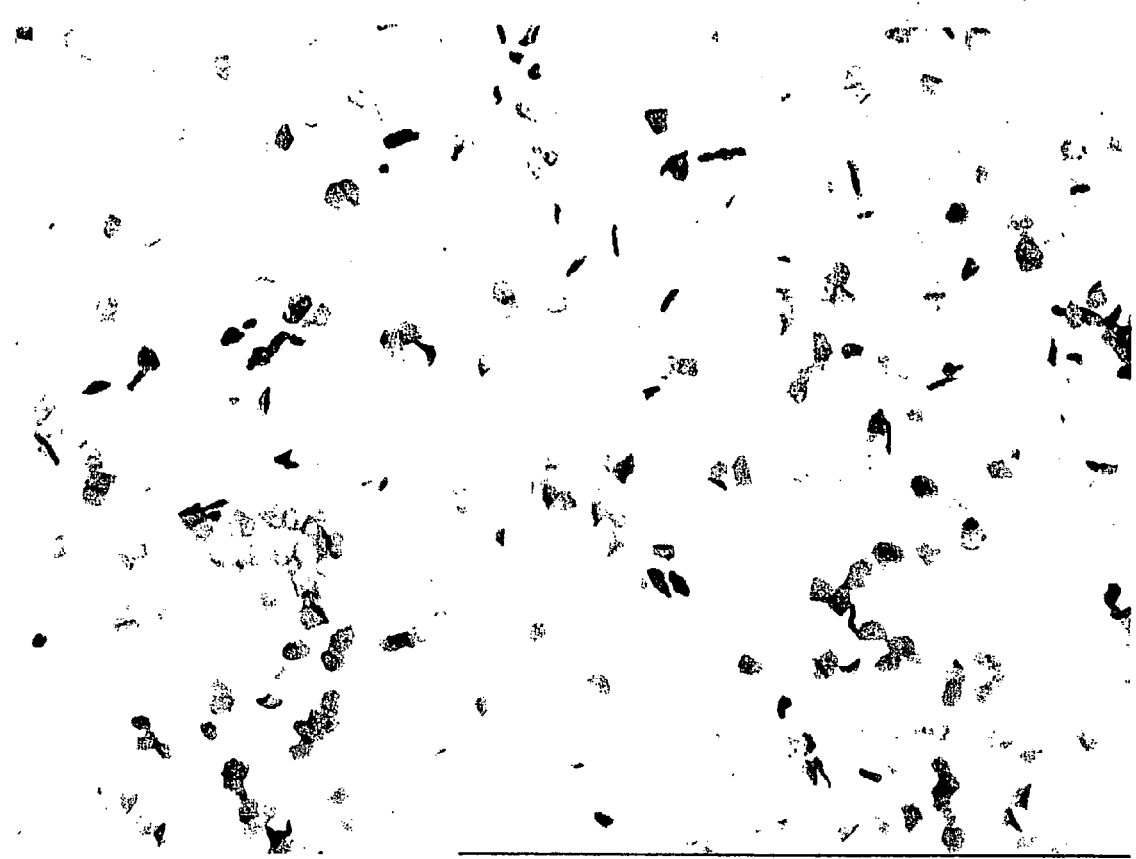
FIG. 3 shows a microscopic photograph of horny cell specimen prepared by the method according to Comparative Example 2 described in Example 1 of the present invention.

Three horny cell samples were prepared from one panelist by stripping corneocites off from the surface of his/her skin using an adhesive tape, and two of them were stained according to the inventive staining method. Particularly, the two samples were immersed in a dyeing solution of 3 wt % gentian violet and 1 wt % brilliant green in an aqueous solution of 20% ethanol for 2 minutes and then washed in water sufficiently. One of them was mounted in an ultraviolet-curing resin and then cured by exposure to UV light (Comparative Example 1) while the other was mounted in dimethicone (silicone) according to the present invention (Example 1). The remaining sample was immersed in a dyeing solution of 1 wt % gentian violet and 0.5 wt % brilliant green in water for 10 minutes, washed in water sufficiently, and then mounted in dimethicone (Comparative Example 2). Microscopic photographs of these samples are shown in FIGS. 1-3. As shown in FIGS. 1-3, a low contrast was obtained due to color running in Comparative Example 1 and the corneocites were less stained in Comparative Example 2 while the corneocites were well stained without color running (i.e., a higher contrast was obtained than that obtained in Comparative Example 1). Those results show that a horny cell specimen obtained by the inventive method can provide clear and distinct visualization of corneocites.

Example 2

Average size was calculated for each of the horny cell specimens obtained by Example 1, Comparative Examples 1 and 2. The image of the horny cell specimen of Example 1 was manually binarized and used to calculate an average size ($\mu m^2$). Twenty cells were averaged for each example. The results are shown in Table 1 below. Those results show that automatic calculation of size gave the same result as the result obtained by manual calculation according to the present invention. On the other hand, automatic calculation of size gave higher values than the actual results for the specimens with less clear staining or color running.

TABLE 1

| SAMPLE | AVERAGE SIZE ± VARIANCE |
|---|---|
| AUTOMATIC DETERMINATION (EXAMPLE 1) | 568 ± 121 |
| AUTOMATIC DETERMINATION (COMPARATIVE EXAMPLE 1) | 721 ± 237 |
| AUTOMATIC DETERMINATION (COMPARATIVE EXAMPLE 2) | 736 ± 175 |
| MANUAL DETERMINATION (EXAMPLE 1) | 559 ± 134 |

Example 3

Similar process was repeated as in Example 1 except for using variable amounts of gentian violet. Again, 1% by weight of brilliant green was used. Dimethicone was used for mountion. The clearness of staining were indicated as: ○=clear; Δ=less clear; X not clear. The results are shown in Table 2 below. Those results show that gentian violet may preferably be present at an amount of 1.5-5% by weight and more preferably 2-4% by weight.

TABLE 2

| CONC. OF GENTIAN VIOLET | STAINING COLOR DEFINITION |
|---|---|
| 1.5% BY WEIGHT | ○~Δ |
| 2.5% BY WEIGHT | ○ |
| 4.5% BY WEIGHT | ○ |

Example 4

Similar process was repeated as in Example 3 except for using variable amounts of brilliant green. Sample used was a specimen of corneocites obtained from an individual whose skin was in a bad condition in which nuclear cells were observed. The clearness degree of nuclear staining was determined as in Example 3. The results are shown in Table 3 below. Those results show that brilliant green may preferably be present at an amount of 0.7-2% by weight and more preferably 0.8-1.5% by weight.

TABLE 3

| CONC. OF BRILLIANT GREEN | STAINING COLOR DEFINITION |
|---|---|
| 0.7% BY WEIGHT | ○~Δ |
| 0.9% BY WEIGHT | ○ |
| 1.5% BY WEIGHT | ○ |

Example 5

Similar process was repeated as in Example 1 except for using variable amounts of ethanol. Additionally, the presence or absence of precipitation (insoluble fraction) of the stain was determined. The clearness of staining was indicated as: ○=clear; Δ=less clear; X not clear. The precipitation was indicated as: "present"; "a small amount"; "absent". The results are shown in Table 4 below. Those results show that water-soluble organic solvent may preferably be present in the liquid solvent at an amount of 3-40% by weight and more preferably 5-30% by weight.

TABLE 4

| CONC. OF ETHANOL | PRECIPITATION | STAINING COLOR DEFINITION |
|---|---|---|
| 1% BY WEIGHT | SMALL AMOUNT | ○~Δ |
| 25% BY WEIGHT | NONE | ○ |
| 30% BY WEIGHT | NONE | ○ |

Example 6

Similar process was repeated as in Example 1 except for using a 20% ethanol solution as the organic solvent. Clearly stained specimen was obtained as in Example 1.

Example 7

Similar process was repeated as in Example 1 except for using a 10% acetinitrile solution as the organic solvent. Clearly stained specimen was obtained as in Example 1.

Example 8

Similar process was repeated as in Example 1 except for using different mounting agents. Color running was indicated as: ○=no running; Δ=some running; X=significant running. The results are shown in Table 5 below. Those results show that oil and fat constituent and/or component that is liquid at 1 atm, 25° C. may preferably be used as an mounting agent for preparing horny cell specimen according to the present invention.

TABLE 5

| ENCAPSULATING AGENT | COLOR-BLEEDING |
|---|---|
| PHEMETHICON | ○ |
| OLEIC ACID OCTYLDO DECYL | ○ |
| GLYCERYL TRIISOOCTANOATE | ○ |
| UV-CURING RESIN | X |
| BALSAM/XYLENE SOLUTION | X |

*OIL AND FAT CONSTITUENT THAT IS LIQUID AT 1 ATM, 25° C.

According to the present invention, methods for staining horny cell and preparing horny cell specimen can be provided which can clearly stain horny cell during shorter period of time and provide useful information for personal consultation quickly.

[3] Skin Analysis System

Embodiment of the skin analysis system according to the present invention will hereinafter be described in reference to attached drawings though the configuration of the inventive system may not be limited to those described in the embodiment.

Figure 4:
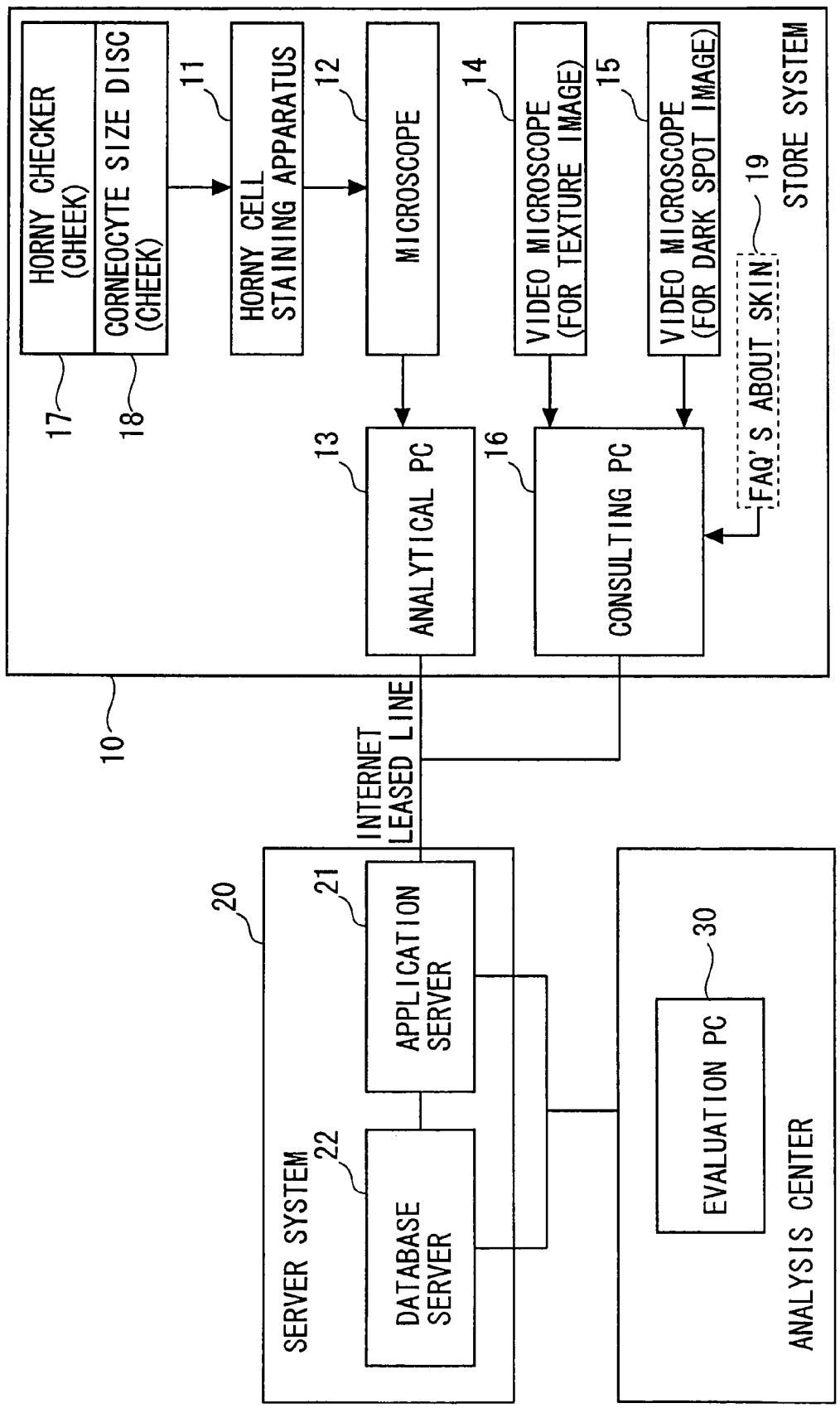
FIG. 4 is a diagram showing one example of the skin analysis system according to the present invention.

FIG. 4 shows an embodiment of the skin analysis system according to the present invention. The skin analysis system shown in FIG. 4 can be used to provide a customer who visits a cosmetic store with a consultation including skin analysis (skin evaluation) of the customer (a subject), provide the customer with an opportunity to purchase a trial kit selected based on the results of the evaluation so that he/she can purchase the cosmetic product(s) contained in the trial kit if he/she likes it (them).

For this purpose, the inventive skin analysis system may comprise a store system or systems 10 which are located in stores, a server system 20 which is connected to the store system or systems 10 via a network (e.g., using an internet leased line over the internet in this example), and an Evaluation personnel computer (Evaluation PC) 30 which may be connected to the server system 20 via a network (e.g., a local area network).

According to the skin analysis system, the following 6 categories may be analyzed (evaluated): "roughness of the surface of keratinized layer (TA)"; "completeness of keratinized layer"; "texture"; "dark spot/color evenness"; "sensitive skin type"; and "tendency to acne".

For this purpose, store system 10 may comprise a horny cell staining device 11, a microscope 12, an analytical personnel computer 13 (Analytical PC), video microscopes 14 and 15, and a consultation personnel computer 16 (Consulting PC).

The horny cell staining device 11 may be used to stain corneocites which have been collected from the surface of the customer's cheek which are then used to analyze the roughness of the surface of keratinized layer or the completeness of keratinized layer of the customer's skin (of a part of face, e.g., cheek). Corneocites may be obtained by stripping off from the surface of the customer's cheek skin using an adhesive material. Any known horny cell checker 17 (e.g., a transparent adhesive tape such as cellophane-tape) or surface area disc 18 (e.g., an adhesive disc comprising a polyethylene terephthalate plate and adhesive coated thereon) may be used. Corneocites may be stained in a solution of stain in solvent containing a water-miscible organic solvent. Therefore, corneocites attached to the adhesive material can be stained directly since the substrate of the adhesive material may not be damaged during the staining step, thereby eliminating the necessity of further transferring the sample to another material for staining. Stains preferably include eosin, hematoxylin, gentian violet, brilliant green and malachite green, which can be used alone or in combination. Among all, a combination of gentian violet and brilliant green may be particularly preferable. This is because that cytoplasm can be stained with gentian violet to obtain a high contrast between the cytoplasm and the background thereby clearly visualizing the shape of corneocites, and that the stained cytoplasm may in turn act as the background so that nuclei of the corneocites can be clearly stained with brilliant green. The sample is stained in a solution of any of such stains in liquid solvent containing a water-soluble (water-miscible) organic solvent. Stain may preferably be present in the dyeing solution at an amount of 2-7% by weight. For a combination of gentian violet and brilliant green, gentian violet may preferably be present at an amount of 1.5-5% by weight and more preferably 2-4% by weight while brilliant green may preferably be present at an amount of 0.7-2% by weight and more preferably at 0.8-1.5% by weight. Examples of water-soluble organic solvent preferably include: alcohol such as methanol, ethanol, isopropanol or 1,3-butanediol; keton such as acetone or methyl ethyl ketone; nitrile such as acetinitrile; and ether such as tetrahydrofuran. Among all, alcohol is preferable and ethanol is particularly preferable. Water-soluble organic solvent may preferably be present in the liquid solvent at an amount of 3-55% by weight and more preferably 5-50% by weight. This is because that a larger amount of organic solvent may not contribute to reduction in the time required for staining or rather may degrade the adhesive or substrate of adhesive material while a smaller amount cannot stain a sample clearly. Under those conditions, it may take 1-5 minutes to stain a sample, which is much shorter than the time required for staining according to conventional methods (10-30 minutes) (using 0.5-1% by weight of gentian violet and 0.2-0.5% by weight of brilliant green). Further, a very high contrast can be obtained. Besides, the staining method using those conditions can be performed at room temperature. Staining may be performed by the person in charge in store using horny cell staining apparatus 11.

Next, the person in charge may prepare a horny cell specimen using the stained corneocites. A horny cell specimen may be prepared by obtaining a horny cell sample containing corneocites which have been stripped off from the surface of skin using an adhesive material, staining the horny cell sample and mounting the stained horny cell sample in an oil and fat component and/or composition that is liquid at 1 atm, 25° C. Examples of oil and fat constituent and/or composition that is liquid at 1 atm, 25° C. may include any oil and fat constituents which are conventionally used in cosmetic products and drugs as well as compositions comprising any combination thereof which are liquid at 1 atm, 25° C. Preferable examples may include one or any combination of two or more selected from the group consisting of silicone oil, fatty acid triglyceride, ester of higher alcohol and fatty acid, and carbohydrate which are liquid at 1 atm, 25° C. Generally, mountion in a liquid component may not provide a stability of 1 month or longer. However, this may not be critical for an instant consultation at a store counter. Such oil base may not cause color running and thus a microscopic image of a specimen obtained can be processed into a binary image (binarization) based on whether the corneocites have been stained or not to visualize the shape of horny cell accurately. Then, the size of horny cell can automatically be computed accurately. Additional information which can be obtained from a specimen prepared by the above-described method include the presence or absence of nuclear cell, the frequency of nuclear cell appearance, the arrangement regularity of corneocites, the shape of horny cell, the roughness of the surface of keratinized layer and the like. The specimen can preferably be used to determine numerical values for those parameters. In summary, horny cell specimens prepared may preferably be used to determine one or more selected from the group consisting of the size of horny cell, the presence or absence of nuclear cell, the frequency of nuclear cell appearance, the arrangement regularity of corneocites, the shape of horny cell and the roughness of the surface of keratinized layer.

Microscope 12 may produce an enlarged image of the horny cell specimen placed thereon at a desired magnification. In this example, the corneocites may be magnified 30 times for evaluating the roughness of the surface of keratinized layer (TA), and 150 times for evaluating the completeness of keratinized layer. Microscope 12 may comprise an image pickup device such as CCD (charge-coupled device). An enlarged image produced by the image pickup device may be then transmitted to Analytical PC 13 via a signal line.

Analytical PC 13 may comprise a CPU, a main memory, an auxiliary memory, a communication control device, an input device (such as a keyboard or a mouse) and an output device (such as a display monitor or a printer). The CPU may load a program obtained from the auxiliary memory into the main memory and run the program to perform the following functions:

(A) to receive enlarged images transmitted from microscope 12 (output signals from the image pickup device) and generate image data for these image (horny cell images (TA) and (completeness)), which corresponds to a horny cell image data generating means;

(B) to determine the size of horny cell using the horny cell image, which corresponds to a measurement means; and (C) to transmit the horny cell image data and the horny cell size determined to server system 20 over the Internet, which corresponds to transmitting means.

Analytical PC 13 may acts as a measurement means to binarize the horny cell image into black and white (monochromatic image of the horny cell is generated). Therefore, the horny cell image may consist of one or more black regions (stained horny cell(s)) and white portion(s) (the background: unstained region(s)). The number of pixel in the black region(s) (horny cell or corneocites) may be determined and the size of horny cell may be calculated from the pixel number. The size may be determined for two or more corneocites in the horny cell image, and the average horny cell size and the number of horny cell to be used to determine the average size may be recorded.

Analytical PC 13 may then act as transmitting means to transmit the image data for each horny cell image as well as information on the average size and the number of corneocites measured to server system 20 over the Internet.

Video microscope 14 may produce an enlarged image (X30) of the surface of a desired part (e.g., cheek) of customer's face for analyzing the texture of the customer's skin, and transmit image signals generated therefrom to Consulting PC 16.

Video microscope 15 may produce an enlarged image (X5) of the surface of a desired part (e.g., cheek) of customer's face for analyzing the dark spot/color evenness of the customer's skin, and transmit color image signals (RGB signals) generated therefrom to Consulting PC 16.

Consulting PC 16 may comprise a CPU, a main memory, an auxiliary memory, a communication control device, an input device (such as a keyboard or a mouse) and an output device (such as a display monitor or a printer). The CPU may load a program obtained from the auxiliary memory into the main memory and run the program to perform the following functions:

(a) to receive image signals from video microscope 14 and generate image data for them (texture image data), which corresponds to a texture image data generating means;

(b) to receive color image signals from video microscope 15 and generate image data for them (original image data) as well as B channel image data, i.e., image data consisting of B channel only extracted from the original image, which corresponds to a dark spot image generating means;

(c) to receive information on the customer's attributes (private data: name, age, address and the like) and answers to questionnaires about skin 19 (FAQ's about skin) including skin troubles which have been entered into Consulting PC 16 using an input device, which corresponds to a reception means;

(d) to transmit image data for the texture evaluation, original and B channel images as well as the manually entered data (e.g., the customer's attributes, answers to FAQ's and others) to server system 20 over the internet, which corresponds to a transmitting means;

(e) to receive the data of web page(s) containing the results of skin analysis from server system 20 over the internet, which corresponds to a receiver means; and (f) to output the received web page(s) to a monitor (an output device) for display (which corresponds to a display control means) or to a printer for printing.

Consulting PC 16 may generate a B channel image (blue light image with peak at 435.8 nm in principle) as an image to be used for dark spot/color evenness analysis. B channel image is known to be useful for detecting melanin granules in a horny cell. Conventionally, corneocites collected from the surface of subject's skin have been stained with silver nitrate and gentian violet to prepare a specimen which was then observed by a microscope to inspect melanin which may cause generation of dark spots (see Japanese Patent Application Laid-Open No. 2000-212037). According to the present invention, a B channel image may be generated using a video microscope 15 to eliminate preparing a specimen for melanin observation, thereby providing results of dark spot analysis more quickly than the prior art.

Horny cell, texture, original and B channel images may be provided in, for example, JPEG standard data (JPEG data) format, or in any suitable image file format such as GIF or WINDOWS BITMAP.

Server system 20 may comprise an application server 21 (which corresponds to a display data generating device) as the display data generating device according to the present invention and a database server (DB server) 22. Application server 21 may comprise a CPU, a main memory, an auxiliary memory, a communication control device and other device or devices. The CPU may load a program obtained from the auxiliary memory into the main memory and run the program. In this way, the application server 21 can perform the following functions:

(I) to receive, from Consulting PC 16 (originally from Analytical PC 13), and store the horny cell image data and the information on the average size and the number of horny cell measured, which corresponds to a receiving means;

(II) to receive and store the texture, original and B channel image data transmitted from Consulting PC 16 as well as the manually entered data including the customer's attributes and answers to FAQs, which corresponds to a receiving means;

(III) to transmit the data and information received from Analytical PC 13 and Consulting PC 16 to Evaluation PC 30;

(IV) to generate data for one or more web pages which contain results of the evaluation obtained based on the data and/or information on the results of the evaluation transmitted from Evaluation PC 30 and on the data and/or information stored in DB server 22, which corresponds to a data generating means; and (V) to transmit the web page data to Consulting PC 16.

DB server 22 may comprise a CPU, a main memory, an auxiliary memory, a communication control device and other device or devices. The CPU may load a program obtained from the auxiliary memory into the main memory and run the program. In this way, DB server 22 may perform the following functions:

(i) to generate and update an aggregate database which is a database that contains accumulated data of the results obtained from skin analysis (evaluation); and (ii) to generate and update a customer database which is a database that contains accumulated results obtained from skin evaluation for each customer.

Before developing the skin analysis system according to the present invention, the present inventors performed a certain skin analysis on hundreds of panelists to examine the roughness of the keratinized layer, the completeness of corneocites, skin texture, dark spot/color evenness and whether sensitive skin type or not, and preserved the data obtained. According to the inventive skin analysis system, DB server 22 stores those data as an aggregate data (mass data) so that those data can be added to the customer's data for comparison.

Evaluation PC 30 may be located at Analysis Center and manipulated by an evaluator at the center. Evaluation PC 30 may comprise a CPU, a main memory, an auxiliary memory, a communication control device and the like. The CPU may load a program obtained from the auxiliary memory into the main memory and run the program. In this way, Evaluation PC 30 may perform the following functions.

Evaluation PC 30 may receive image data for horny cell images (TA) and (complatenes), a texture image and a B channel image as well as information on the average size and number of horny cell measured from Application server 21, and display the data and information on a display device (a display monitor). The evaluator may evaluate TA and completeness by referring to the horny cell images (TA) and (completeness) displayed on the display monitor as well as taking into consideration the average size and number of horny cell measured. The evaluator may also evaluate the texture of skin by referring to the texture image displayed on the display monitor. Further, the evaluator may also evaluate dark spot/color evenness by referring to the B channel data on the display. TA, completeness, texture, dark spot and color evenness may be evaluated based on, for example, a 10-point scale evaluation. Evaluation PC 30 may generate information on those results of the evaluation which may be then transmitted to application server 21.

Once application server 21 receives the results of the evaluation from Evaluation PC 30 it may produce a web page containing those results. For example, application server 21 may produce data for a web page which may contain the results of the evaluation received from Evaluation PC 30 (a web page in the detailed analysis zone described later). In this step, when data of the customer's past results have been preserved in the customer database in DB server 22, those data may be obtained and used to determine the average of the customer's past data (described later) which may be then included in the web page.

Application server 21 may perform a total evaluation on the results obtained by current skin analysis of the customer according to a predetermined principles based on the results of the evaluation transmitted from Evaluation PC 30, determine a total skin score, position and the like (described later), and generate data for a web page showing them. In this step, an aggregate data on the results obtained for those of the same generation may be obtained from the aggregate data base in DB server 22 and used to create a web page so that the results of the evaluation of the customer can be, compared to the aggregate data. When the customer' previous data are preserved in the customer database in DB server 22, the data may be obtained and included in the web page as the previous data (described later).

Moreover, application server 21 may determine advice on skincare (skincare advice), product or products recommended to be used for skincare (cosmetic products) and a trial kit based on the results of the evaluation, and produce a web page which presents those information.

Data materials to be used for producing the above-described web page (e.g., HTTP file, XML file, image/dynamic image/audio file or the like) may have already been prepared in the auxiliary memory of application server 21. Application server 21 (or the CPU thereof) may produce a web page using the data components. In this step, the horny cell, texture, original and B channel images and/or other data received from Consulting PC 16 may be used as components of the web page. Various web pages which each present different cosmetic products or trial kits may be prepared in the auxiliary memory of application server 21 (or DB server 22), and suitable one may be selected among these pages according to the recommended skincare procedure determined based on the results of the evaluation for the customer.

In this way, application server 21 may construct a web site consisting of a plurality of web pages showing the results of skin analysis (results of the evaluation) and transmit the data for those web pages to Consulting PC 16 over the internet.

The results of the evaluation of the current skin analysis displayed on the web pages may be accumulated in the customer database of DB server 22 as well as in the aggregate data base as a part of aggregate data.

Application server 21 may supply the results of skin analysis obtained for the customer in a web system format to Consulting PC 16. In summary, a plurality of web pages containing information such as skin analysis results may be transmitted to Consulting PC 16 over the Internet. Once Consulting PC 16 receives those web pages, a web browser (a display control means) installed in Consulting PC 16 may display each page on the screen monitor. The customer can receive the skin analysis results, advice on skin treatment and explanation about cosmetic products which are recommended to the customer by referring to the web pages.

Figure 5:
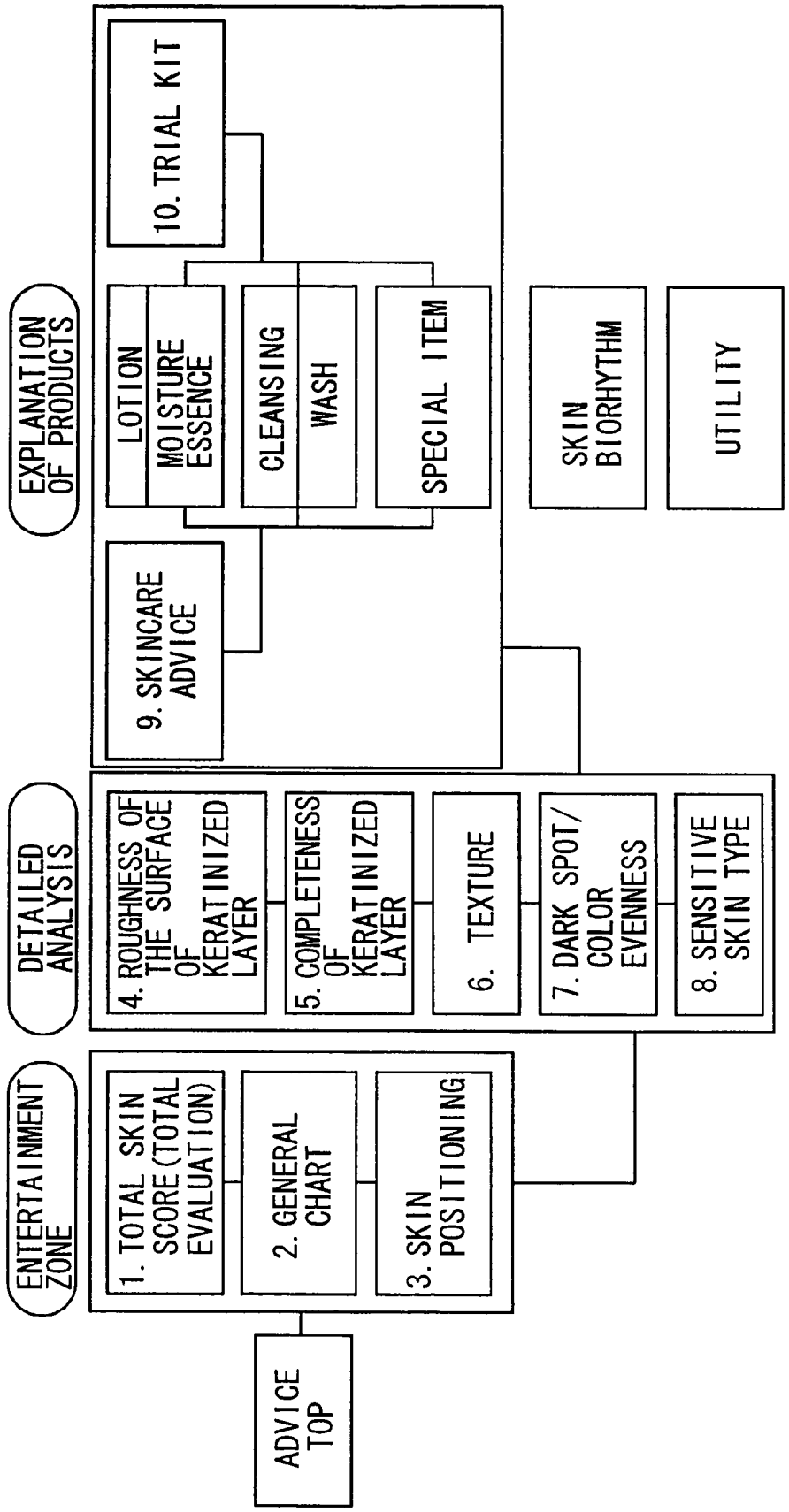
FIG. 5 is a block diagram showing a plurality of web sites to be provided to a customer.

FIG. 5 is a block diagram of a web site (referred to as "advice site") consisting of a plurality of web pages which will be provided to a customer, showing a plurality of different web pages and the relationship of the linkages therebetween. In FIG. 5, the advice site may comprise an entertainment (introduction) zone, a detailed analysis (laboratory) zone, and a product explanation (cosmetic information) zone.

The entertainment zone may consist of web pages each titled "1. total skin score (total evaluation)", "2. general chart" and "3. skin positioning". The detailed analysis zone may consist of web pages titled "4. roughness of the surface of keratinized layer", "5. completeness of keratinized layer", "6. texture", "7. dark spot/color evenness" and "8. sensitive type". The product explanation zone may consist of web pages titled "9. skincare advice" and "10. trial kit". The advice site may further contain web pages titled "11. skin biorhythm" and "12. utility".

Figure 6:
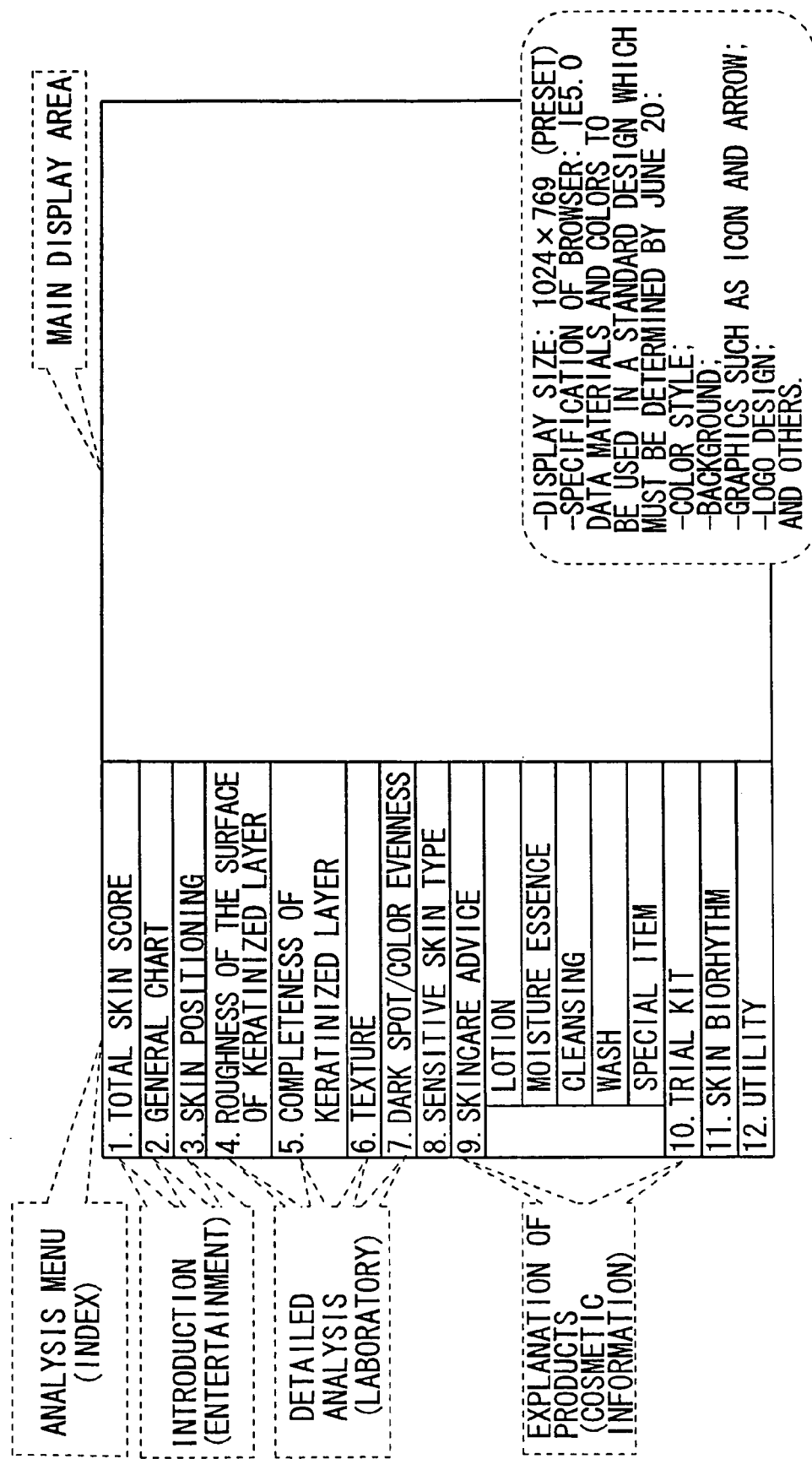
FIG. 6 is an explanatory diagram of a screen representation displayed on a web page.

FIG. 6 is an explanatory view of a web page representation. In FIG. 6, specifications of the web page representation are provided in the box (dashed line) (similarly in FIGS. 7-22). As shown in FIG. 6, a menu list area showing the list of web page titles (analysis menu) is provided on the left side of the page screen. Indexes for web pages Nos. 1-12 (shown in FIG. 5) are provided in the menu list area. Each index may function as the icon for shortcut to the designated web page and can be selected by using an input device (a keyboard or a mouse). Once a particular index is selected, the selected index may be highlighted and indicates the current location on the advice site. The menu list area may be permanently displayed at the advice site. A main display area may be provided on the right side of the menu list area. Each of web pages Nos. 1-12 may be alternately displayed in the main display area.

FIG. 7 shows one example of the top (title) web page of the advice site. In this page, the title of the advice site, customer's name, customer's identification information (ID), and date of test are shown in the main display area. Each of customer's name, ID and date of test columns may also function as an entry space for those information.

Figure 8:
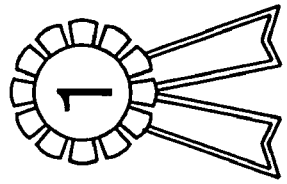
FIG. 8 shows one example of a screen representation displayed on a web page titled "1. total skin score (total score)"

FIG. 8 shows one example of web page titled "1. total skin score (total evaluation)". Customer's name, his/her total skin score (the total score obtained by evaluation of horny cell) and skin positioning (which indicates the ranking of the results of the evaluation). "Noble skin" is one of the zone names indicating horny cell rankings.

Figure 9:
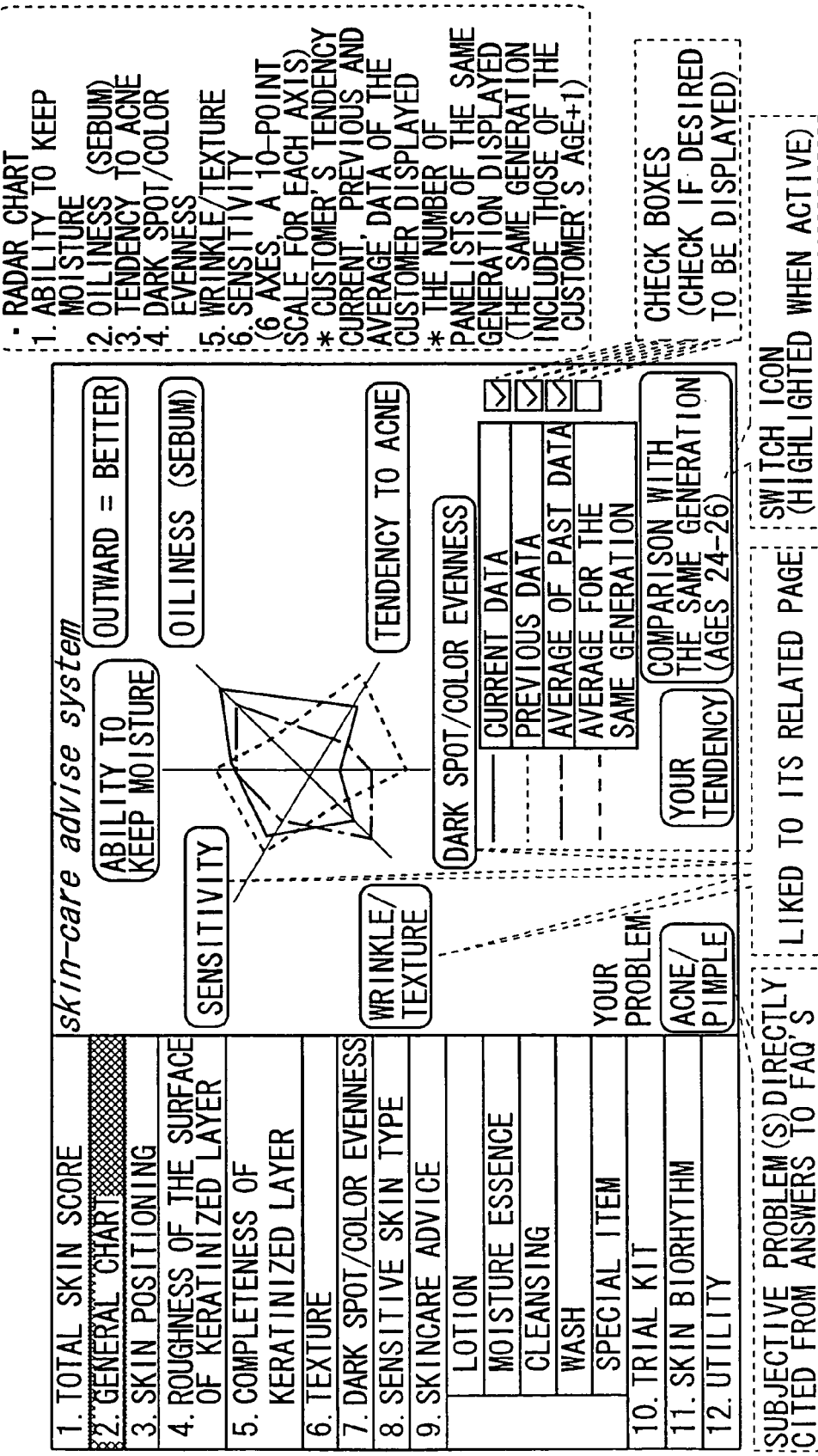
FIG. 9 shows a first example of a screen representation displayed on a web page titled "2. general chart"

FIG. 9 shows one example of a first web page titled "2. general chart". In the first web page, the main display area may provide a radar chart showing the tendency of the customer's skin. The radar chart may show a 10-point scale evaluation for each of 6 categories: "ability to keep moisture"; "oiliness (sebum)"; "tendency to acne"; "dark spot/color evenness"; "wrinkle/texture"; and "sensitive skin type". Each category column located at the end of an extended line of each axis of the radar chart may function as a shortcut icon linked to the associated page. Particularly, when one category column is clicked by a mouse, the screen may jump to the corresponding web page (any one of web pages Nos. 4-8) in the evaluation analysis zone. The main display area may also contain check-boxes "Current data", "Previous data", "Average of past data" and "Average for the same generation" at its lower right. The representation of the radar chart may be selectively changed by checking these check boxes. "Current data" indicates the results obtained by the current skin analysis of the customer, "Previous data" indicates the result from the previous skin analysis, and "Average of past data" indicates the average of the results obtained for each category in the past skin analyses. The "same generation" refers to people of ages of a predetermined range with respect to the customer's age (for example, the customer's age ±1 or 2, and, in this example, the customer's age ±1). Accordingly, "Average of the same generation" indicates the average of results obtained for each category obtained from the mass data (aggregate data) based on such skin analyses performed on a large number of people of the same generation. The main display area may also provide the number of the aggregate data sample used to determine the "average of the same generation". "Your skin type" and "Comparison with the same generation (ages 24-26)" icons are provided under the check boxes. "Your skin type" icon may be a switch icon to the first page from the second page (i.e., make the first page active) while "Comparison with the same generation (ages 24-26)" icon maybe a switch icon to the second page from the first page (i.e., make the second page active). One of these switch icons which is currently active may be highlighted (i.e., displayed in a deeper color), thereby indicating which page is currently active. In the first page, "Your skin type" icon may be highlighted. Further, problem items checked by the customer in his/her answers to the FAQ's (subjective symptoms cited directly from the answer) may be displayed as "Your problem (s)" in the lower left of the main display area. In this way, the customer can instantly recognize his/her positioning relative to the mass data or determine if his/her skin conditions have been improved by comparing his/her "current data" with "previous data", "average of past data" and "average for the same generation" displayed on the radar chart.

FIG. 10 shows one example of a second web page titled "2. general chart". In the second page, the main display area may illustrate a graph showing the comparison between the customer's current data with the average data for the same generation. In this graph, the center axis indicates the average for the same generation, and the customer's data on each of 6 categories obtained in current skin analysis are shown in relation to the average. Particularly, a bar which extends into one direction (e.g., into the right in FIG. 10) may indicate a result superior to the average while a bar which extends into the other direction (e.g., into the left in FIG. 10) indicates a result inferior to the average in the bar graph. Results of the evaluation for the customer may be expressed in a 10-point scale (5 scales for superior and inferior each). In the main display area on the second page, symbols may be provided in the vicinity of the respective categories so that whether the results for the customer are superior or inferior to the average for the same generation can be recognized easily. In this example, categories for which superior results have been obtained may be marked with "sun (fine)" mark, relatively inferior with "cloud (cloudy)" mark, and much inferior with "umbrella (rainy)" mark. Under the graph, the range of age (in this example, ages 24-26 with respect to age 25, the customer's age) and the number of samples from which the average has been obtained may be provided. Below those information, switch icons are provided which are similar to those in the first page so that the second page can be reversibly switched to and from the first page. In the second page, the "comparison with the same generation" icon may be highlighted when compared to the "your tendency".

Figure 11:
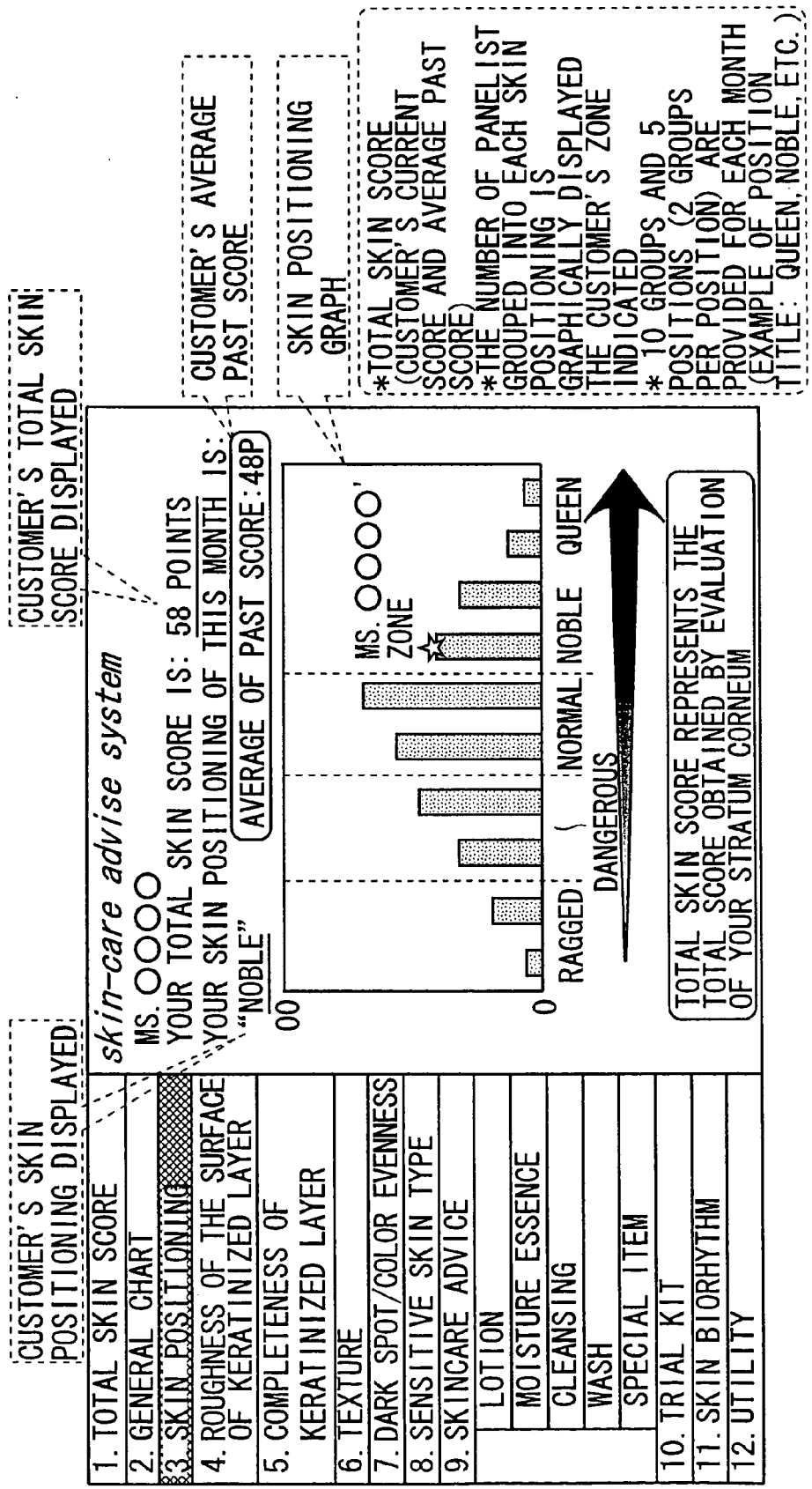
FIG. 11 shows an example of a screen representation displayed on a web page titled "3. skin positioning"

FIG. 11 shows one example of a web page titled "3. skin positioning". In the main display area on this page may be provided a total skin score and a skin position determined in the present skin analysis for the customer as well as his/her average data of the past skin analysis. A "total skin score" is the sum of the points determined for the respective 6 categories in a skin analysis and indicates the total result of the customer's skin horny cell. A "skin positioning" may indicate the location (rank) where the customer's total result of the skin analysis (i.e., skin condition) is located in the distributions of the results for the same generation, which may be represented in a 10-position scale (divided in 10 groups) with 5 positions (2 scales for each position), each titled, for example, "ragged", "dangerous", "normal", "noble" and "queen" (sequentially from the worst to the best) in this embodiment. Past average score may comprise the average of at least 2 skin analyses which have been performed on the customer in the past. In the main display area, a skin positioning graph may also be provided which indicates the distribution of skin positioning obtained for panelists of the same generation. The customer's skin positioning (zone) maybe provided in the skin positioning graph. Such a skin positioning graph may be prepared and displayed with the reference (average) data of the corresponding month (i.e., such reference averaged at a may be prepared for each month) since the skin condition may change corresponding to seasonal change. Therefore, the panelist's data obtained during the same month as the date of the current analysis may be extracted from the aggregate data and used to prepare the skin positioning graph.

Figure 12:
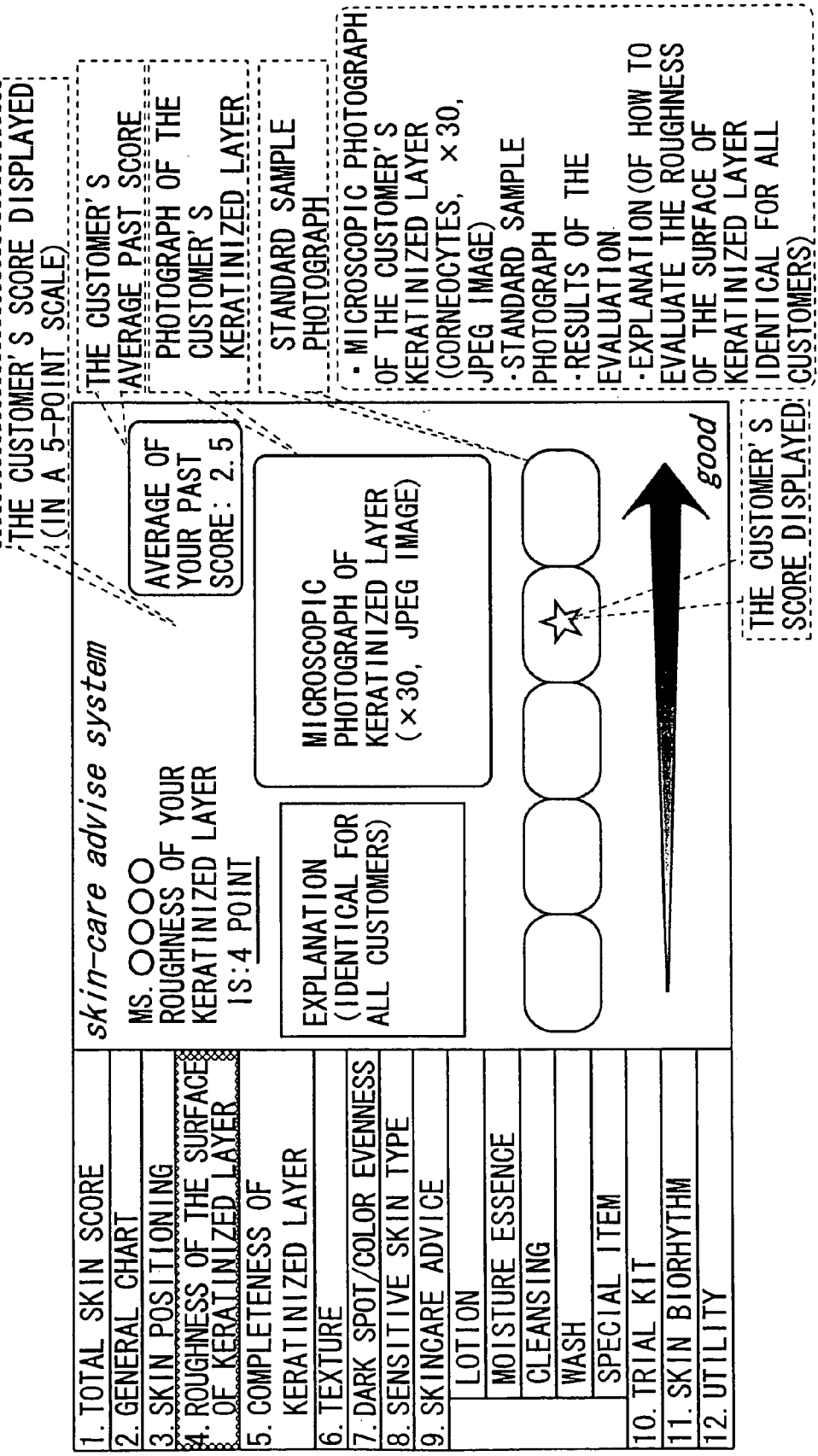
FIG. 12 shows an example of a screen representation displayed on a web page titled "4. roughness of the surface of keratinized layer (the ability of corneocites to keep moisture)"

FIG. 12 shows an example of a web page titled "4. roughness of the surface of keratinized layer (the ability of keratinized layer to keep moisture)". In the main display area on this page may be provided a score (represented in a 5-point scale) determined on the roughness of the surface of keratinized layer observed in the customer as well as the average of his/her past scores. A microscopic photograph (X30) of the customer's keratinized layer may also be provided in the main display area. The microscopic photograph may be an image reproduced from the image data (JPEG data) for an enlarged image of the customer's corneocites which has been obtained by microscope 12 and processed in Analytical PC 13. Information on how to evaluate the roughness or the like may be provided in the vicinity of the microscopic photograph. The customer's score and a standard sample photograph may also be provided in the main display area.

Figure 13:
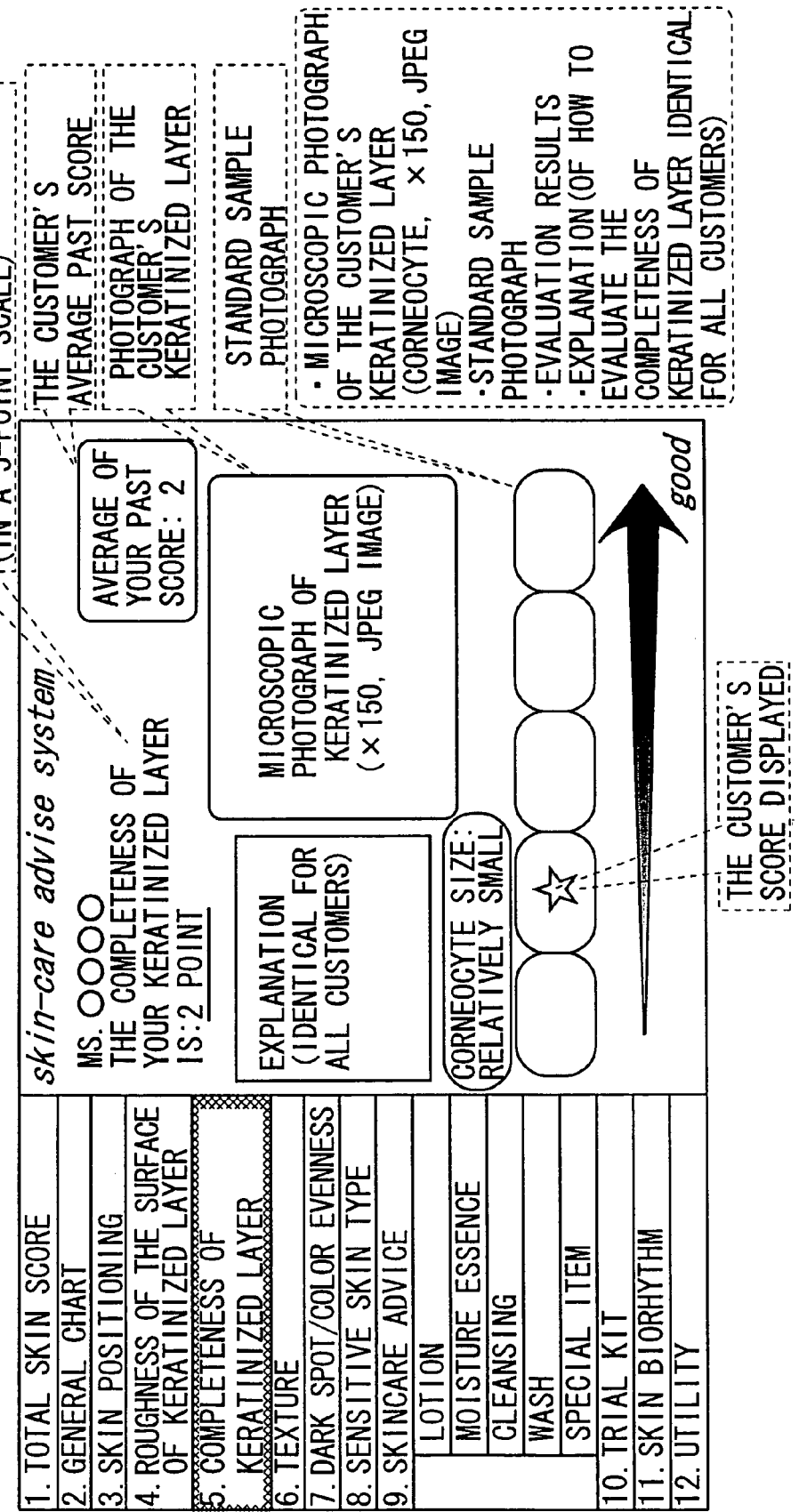
FIG. 13 shows an example of a screen representation displayed on a web page titled "5. completeness of keratinized layer"

FIG. 13 shows one example of a web page titled "5. completeness of keratinized layer". In the main display area on this page may be provided a score (represented in a 5-point scale) determined on the completeness of the customer's keratinized layer as well as the average of his/her past scores. A microscopic photograph (X150) of the customer's keratinized layer may also be provided in the main display area. The microscopic photograph may be an image reproduced from the image data (e.g., JPEG data) for an enlarged image of the customer's corneocites which has been obtained by microscope 12 and processed in Analytical PC 13. Information on how to evaluate the completeness of keratinized layer or the like may be provided in the vicinity of the microscopic photograph. The customer's score and a standard sample photograph may also be provided in the main display area. Further, the horny cell size of the customer may also be provided.

Figure 14:
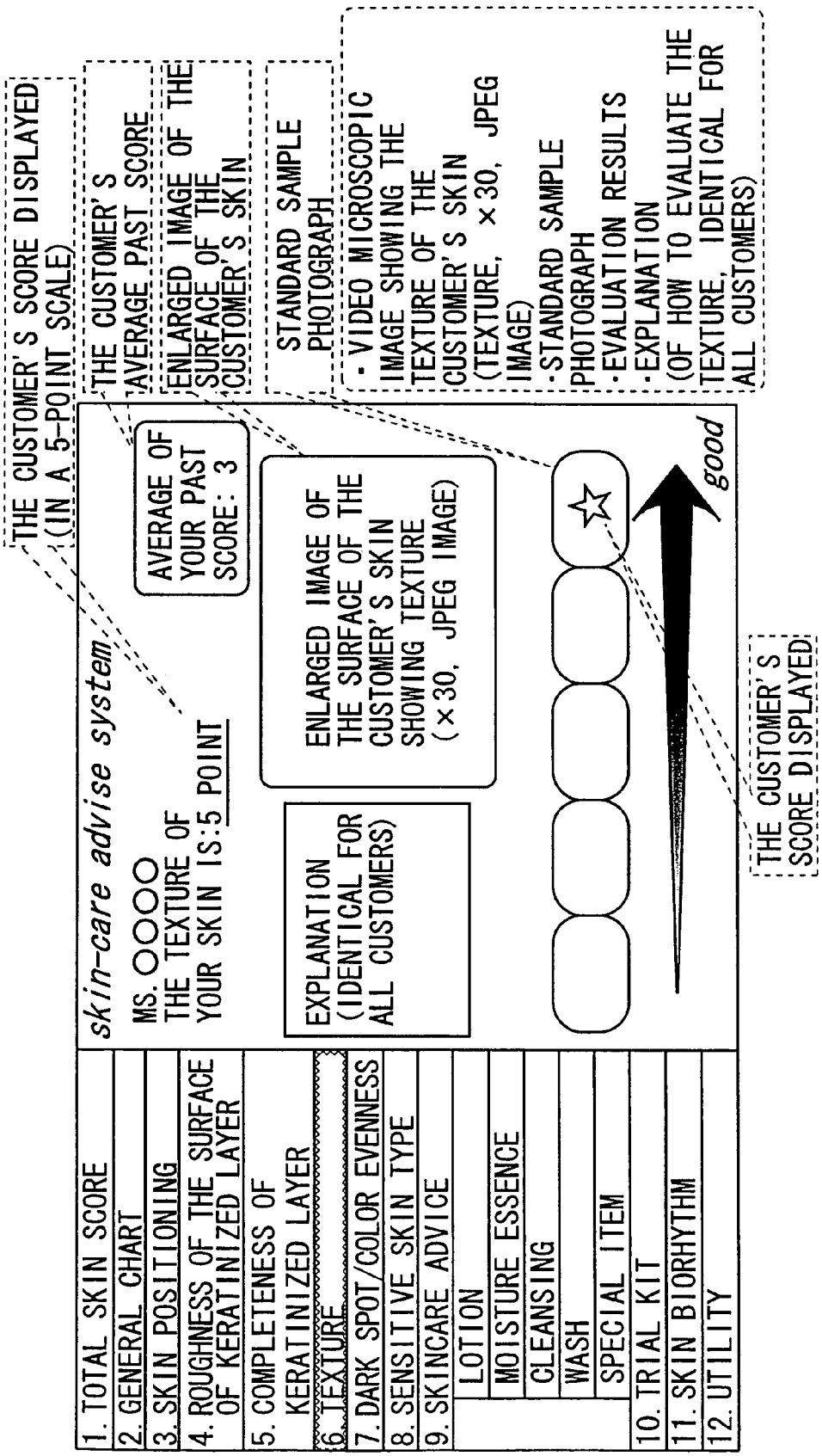
FIG. 14 shows an example of a screen representation displayed on a web page titled "6. texture"

FIG. 14 shows one example of a web page titled "6. texture". In the main display area on this page may be provided a score (represented in a 5-point scale) determined on the texture of the customer's skin (texture condition) observed in the present analysis as well as the average of his/her past scores. An enlarged photograph (X30) of the customer's skin surface showing its texture may also be provided in the main display area. This enlarged photograph may be an image reproduced from the image data (e.g., JPEG data) for an image of the surface of the customer's skin obtained by video microscope 14 and processed in Consulting PC 16. Information on how evaluate the texture condition or the like may be provided in the vicinity of the microscopic photograph. The customer's score and a standard sample photograph may also be provided in the main display area.

Figure 15:
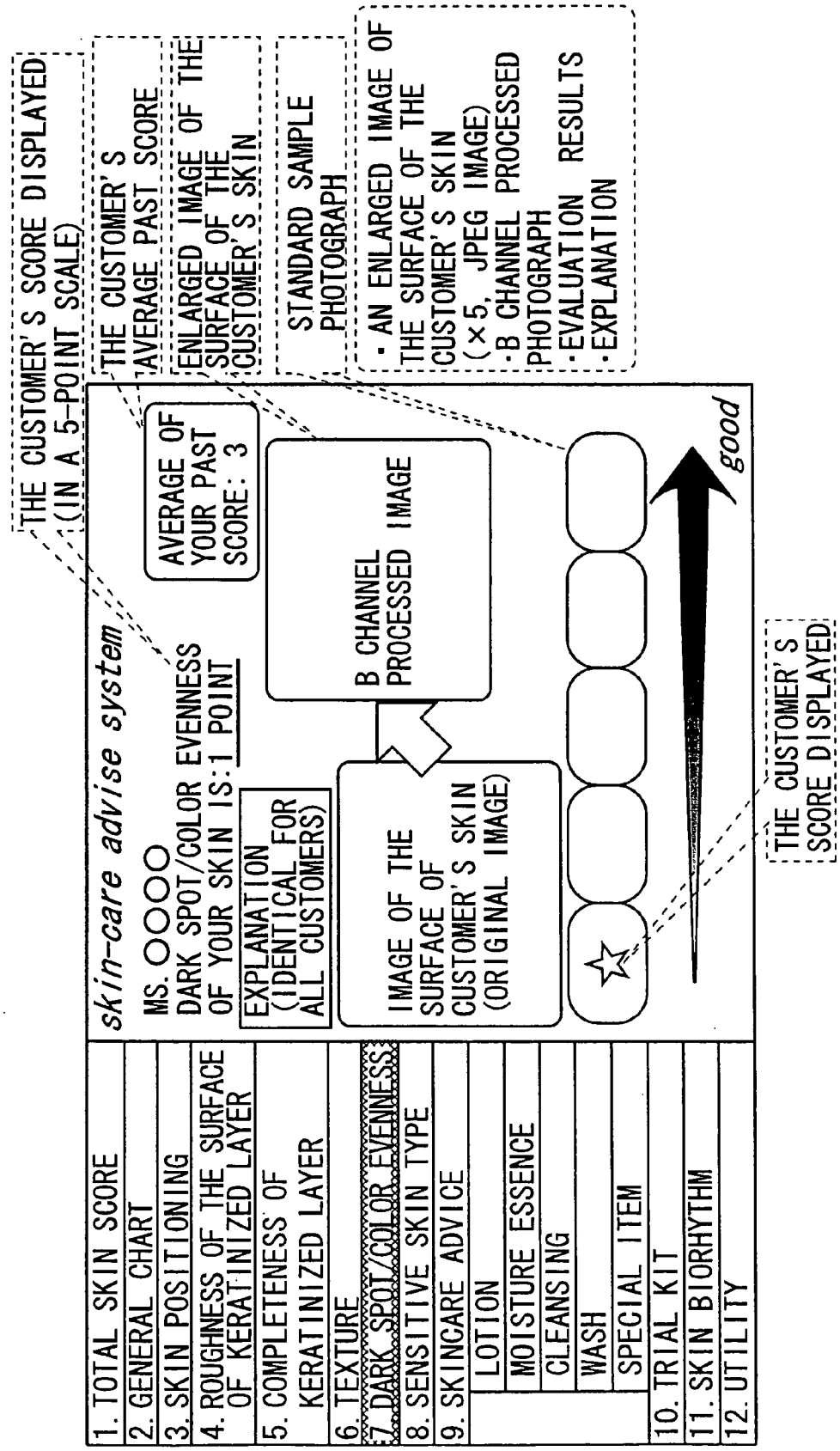
FIG. 15 shows an example of a screen representation displayed on a web page titled "7. dark spot and color evenness"

FIG. 15 shows one example of a web page titled "7. dark spot/color evenness". In the main display area on this page may be provided a score (represented in a 5-point scale) determined on the dark spot/color evenness observed in the current analysis as well as the average of his/her past scores. An RGB color photographic image (original image: X5), which is an enlarged image of the customer's skin surface and a photographic image (B channel image) comprising B channel extracted from the RGB color image may also be provided in the main display area. The original and B channel images may be images reproduced from image data (e.g., JPEG data) for an enlarged image of the surface of the customer's skin which have been obtained by video microscope 15 and processed in Consulting PC 16. Information on how to evaluate dark spot/color evenness or the like may be provided in the vicinity of the original and B channel images. The customer's score and a standard sample photograph may also be provided in the main display area.

Figure 16:
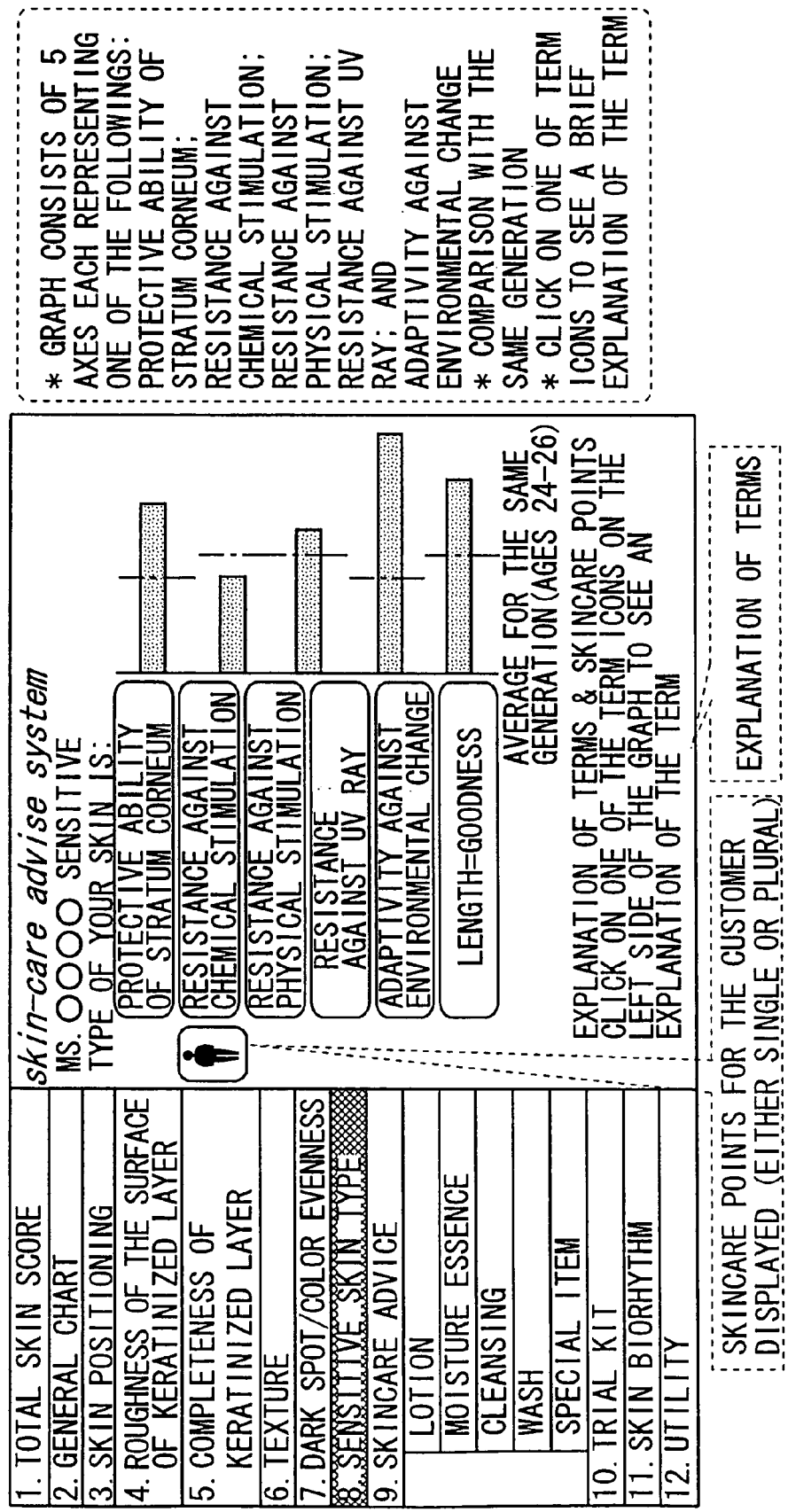
FIG. 16 shows an example of a screen representation displayed on a web page titled "8. Sensitive skin type"

FIG. 16 shows one example of a web page titled "8. sensitive skin type". In the main display area on this page may be provided 5 categories as indicators indicative of sensitive skin type, including "a protective ability of keratinized layer", "resistance against chemical stimulation", "resistance against physical stimulation", "resistance to UV-light", and "adaptivity to environmental change" as well as a graph which show the results on the respective categories obtained for the customer. In the graph, a higher (longer) bar means a better result. In FIG. 13, a longer the bar which extends into the right direction indicates a better result. Average for the same generation may be indicated by dotted line for each category in FIG. 13. Particularly important category or categories for skincare for the customer may be marked with a symbol indicating as such in the vicinity of the category or categories. Further, each category title provided in the main display area may act as the shortcut icon to the corresponding explanatory page which explains the term and the reason on which the results of the evaluation is based. Jumping to the explanatory page of any desired category can be executed by clicking on a jumping icon by using a mouse.

Figure 17:
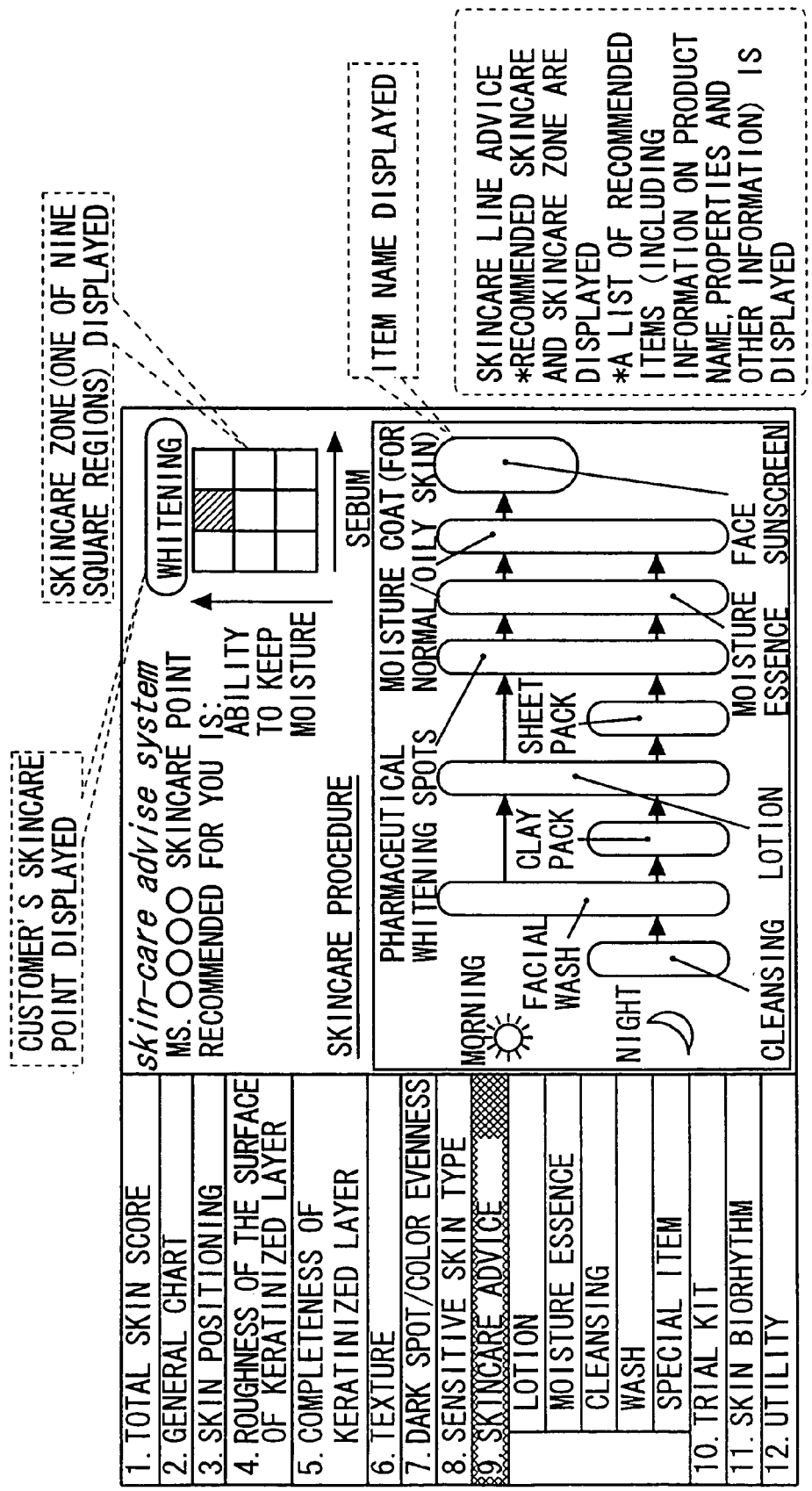
FIG. 17 shows an example of a screen representation displayed on a web page titled "9. skincare advice"

FIG. 17 shows one example of a web page titled "9. skincare advice". In the main display area on this page may be provided important point (s) on skincare (treatment) recommended for the customer (in this example, "whitening" care). The mutual relationship of 2 parameters (indicators) "an ability to keep moisture" and "sebum" may be schematically shown by a matrix consisting of 9 regions (skincare zones). In this matrix, the zone which corresponds to the customer's result may be highlighted. A flow chart showing an appropriate skincare procedure (skincare line) may also be provided in the main display area. The name of item is indicated in a block representing for each step. Each of those blocks may act as a shortcut icon to the introduction page of cosmetic product(s) (which correspond(s) to the item name indicated in the block) which is(are) recommended for use in the step.

Figure 18:
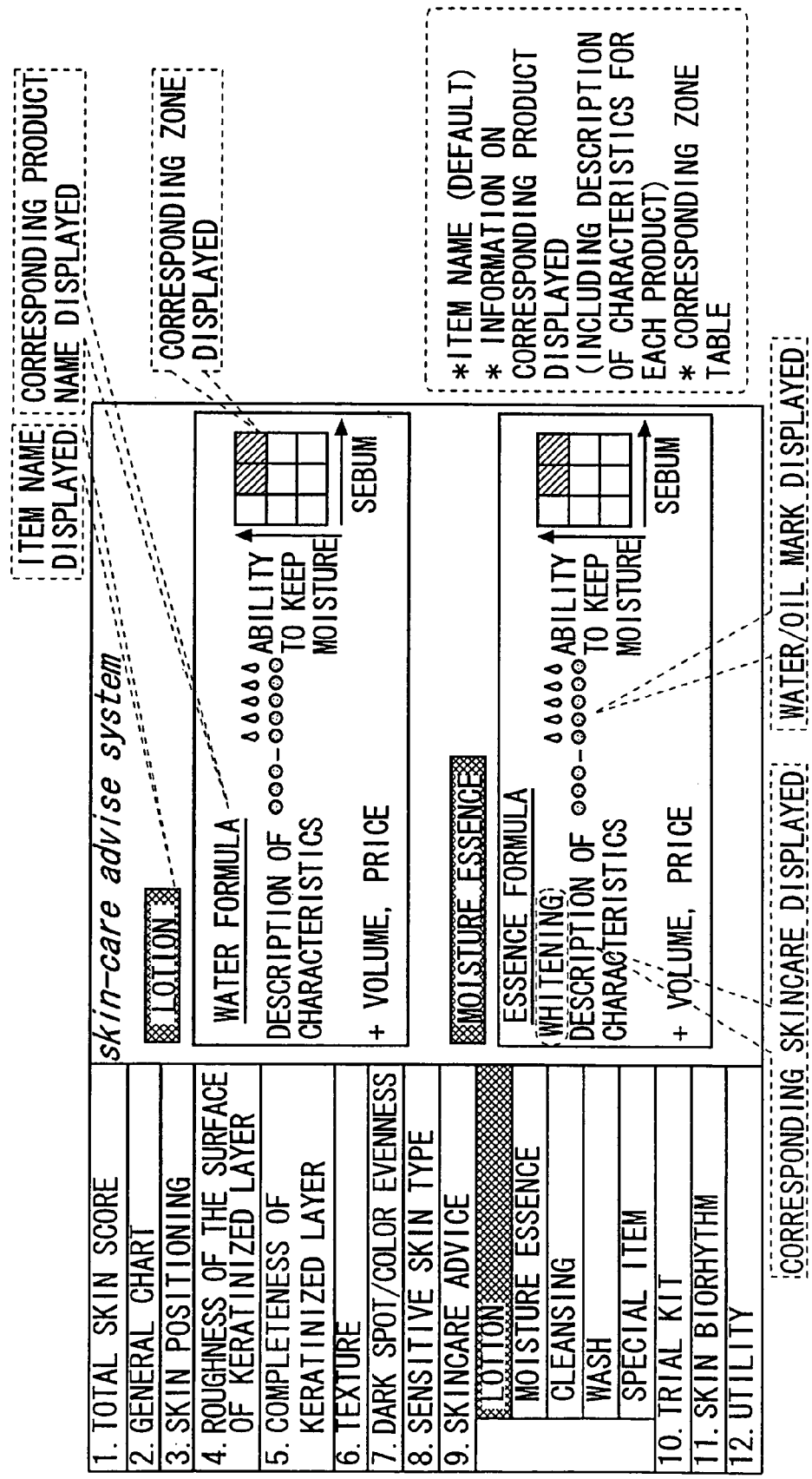
FIG. 18 shows an example of a screen representation displayed on a web page which presents cosmetic products to be used in "lotion" and "moisture essence" steps.

FIG. 18 shows one example of a web page which introduces cosmetic products to be used in "lotion" and "moisture essence" steps. This page corresponds to the page displayed after jumping executed by clicking on either "lotion" or "moisture essence" icon in the flow chart shown in FIG. 17. In this page, particular cosmetic products recommended for the customer to used in "lotion" and "moisture essence" steps as well as the properties, volumes, prices and water/oil mark of the products, and the skincare zones covered by the respective products may be presented.

Figure 19:
FIG. 19 shows an example of a screen representation displayed on a web page which presents cosmetic products to be used in "cleansing" and "(facial) wash" steps.

FIG. 19 shows one example of a web page which introduces cosmetic products to be used in "cleansing" and "(facial) wash" steps. This page corresponds to the page displayed after jumping executed by clicking on either "cleansing" and "facial washing" icons in the flowchart shown in FIG. 17. In this page, particular cosmetic products recommended for the customer to use in "cleansing" and "facial wash" steps as well as the properties, volumes, prices and water/oil mark of the products, and the skincare zones covered by the respective products may be presented.

FIG. 20 shows one example of a web page which introduces cosmetic products to be used as "special item(s)". This page is an introduction page of cosmetic products which are recommended as special items in the flow chart shown in FIG. 17. Those special items correspond to "moisture coat", "pharmaceutical whitening spots" and "clay pack" in the flow chart shown in FIG. 17. Therefore, this page may be displayed after jumping executed by clicking on either one of these item blocks. In this page, particular cosmetic products recommended for the customer to use in "moisture coat", "pharmaceutical whitening spots", "clay pack cleansing", and "additional items" steps as well as the properties, volumes, prices and the like thereof may be provided.

FIG. 21 shows one example of a web page titled "10. trial kit". This page may introduce a trial kit which contains a combination of cosmetic products recommended for the customer which have been selected based on the results of skin analysis. In this embodiment shown in FIG. 21, information on the trial kit recommended may be displayed which include the product names, properties, volumes, water/oil mark or other information of the cosmetic products corresponding to "lotion", "moisture essence" and "facial wash" as well as the price of the trial kit.

FIG. 22 shows one example of a web page titled "11. skin biorhythm". In the main display area on this page may be provided a time-course graph showing the change in the customer's skin condition based on the 6 categories in skin analysis during one year and, for comparison, a corresponding reference graph showing the average of the results obtained for the same generation. Check boxes for the respective 6 categories may also be provided in the main display area. When one of these 6 categories is checked, two graphs each representing the customer's results on the checked category and the corresponding average results for the same generation regarding that category may be displayed. It may be required that the customer take a skin test periodically to prepare such a reference graph.

According to the above-described skin analysis system, the following operation may be performed in store. When a customer takes a skin test in store using store system 10, the customer may have to remove make-up and then his/her corneocites may be collected and/or an enlarged image of the surface of a portion (cheek) of his/her face skin may be obtained.

Next, the counselor (adviser) at the store counter may provide a questionnaire to the customer. The customer may give answers to the questionnaire including the customer's attributes and answers to the FAQ's about skin 19 (including skin problems). These answers may be input in Consulting PC 16. The input information may be automatically transmitted to server system 20.

Then, the counselor may obtain enlarged images (X30 and X5) of the surface of the customer's cheek using video microscopes 14 and 15. These images may be transmitted to Consulting PC 16 which may then produce image data of texture, original and B channel images based on these images and then transmit those data to server system 20 automatically.

Next, the counselor may inspect the customer's corneocites. Particularly, horny cell checker 17 and/or size disc 18 may be brought into contact with his/her cheek to strip corneocites off therefrom to collect a horny cell sample which is then stained in horny cell staining device 11 to prepare a horny cell specimen which may in turn be placed on microscope 12. Then, enlarged images of corneocites obtained at desired magnifications (X 30 and X150) by microscope 12 may be then transmitted to Analytical PC 13 where the average size and number of horny cell observed may be determined. Those data may be then transmitted together with the horny cell images to server system 20 automatically.

In a short time, Consulting PC 16 may receive web page data from server system 20 and display the web page on its display monitor. The counselor and/or the customer can see any one of web pages 1-12 as desired by using the input device connected to Consulting PC 16. In this way, the customer can receive his/her total skin score, general chart, skin positioning, results of detailed analysis or evaluation as well as an explanation of products.

The counselor may give additional advice to the customer while showing the web pages to the customer. The customer may purchase a trial kit selected according to the advice provided on the web page and can try it there. After using the trial kit, the customer can purchase a full size product or products of any items contained in the trial kit if he/she likes it/them since the volume of products in such a trial kit is very small. Alternatively, the customer can purchase any product or products introduced in the skincare procedure recommended for the customer without using a trial kit containing it/them.

The time required from the cleansing to provision of the results of analysis (i.e., web pages from page 1) may be reduced to 30 minutes by employing the above-described methods for staining horny cell and preparing specimen as well as production of B channel image. Therefore, the customer can receive the results of skin analysis, advice on skin care procedure determined according to those results and an explanation of the cosmetic product(s) to be used in the recommended skincare procedure on the day he/she visits the store. With such convenience, customers may have more opportunities to purchase cosmetic products, and therefore the sales of cosmetic products may be promoted.

The customer's data on his/her results of the evaluation may be provided to the customer together with reference data prepared from analysis performed on those of the customer's age ±1 or 2 (average data for the same generation) such that those data can be compared to each other (see FIGS. 9, 11 and 16). Alternatively, the customer's results may be provided to him/her which are represented in relation to results for the same generation (see FIG. 10). Therefore, the customer can know his/her skin condition more specifically.

The results of the evaluation for the customer may be then stored in DB server 22 every time so that the previous data may be displayed together with the current results of the evaluation (see FIG. 9). This may allow the customer to know if his/her skin condition has been improved or not. The customer can also know much more detail about his/her skin condition by referring to the average of his/her past data for each category. Further, from his/her past data, a time-course pattern of change in the customer's skin condition may be provided as a skin biorhythm in comparison with the average pattern for the same generation (a standard pattern), by which the customer can know his/her skin condition more specifically.

Server system 20 may produce web pages containing those results of the evaluation and results of the evaluation for each customer may be stored in server system 20. Therefore, total management of the results of the evaluation for all the customers may be possible even when a plurality of store systems 10 are located at different stores.

The skin analysis system according to the present invention may allow for a quick and clear staining of corneocites as well as quick acquisition of information useful for consultation.

What is claimed is:

1. A skin analysis system, comprising:
   a staining apparatus for staining a sample containing corneocytes stripped off from a skin surface of a subject using an adhesive material comprising a stain solution comprising gentian violet of 2-4% by weight and brilliant green of 0.8-1.5% by weight, and a water-miscible organic solvent of 3-55% by weight, wherein the skin surface is immersed in the stain solution for 1-5 minutes;
   a microscope for obtaining an enlarged image of a corneocytes specimen prepared from the sample stained in said staining apparatus;
   corneocytes image data generating means for generating corneocytes image data that is image data of the enlarged image of the corneocytes specimen obtained by said microscope;
   measurement means for measuring size of a horny cell using said corneocytes image data, wherein the measuring size of a horny cell is conducted by automatic computation;
   transmitting means for transmitting to a server via a network the corneocytes image data and information representing the size of the horny cell obtained by said measurement means;
   receiving means for receiving from the server via the network evaluation information representing results obtained by evaluating at least one of roughness of a keratinized layer surface and arrangement regularity of corneocytes indicating completeness of the keratinized layer based on the corneocytes image data and the information representing the size of the horny cell; and
   display control means for displaying the evaluation information on display means.

2. The system according to claim 1, wherein said microscope creates a magnified image of the corneocytes specimen which includes the stained sample mounted onto an oil and fat constituent and/or component that is liquid at 1 atm, 250° C., and said generating means generates the corneocytes image data of the magnified image.

3. The system according to claim 1, further comprising texture image data generating means for generating texture image data that is image data of an enlarged image of the subject's skin surface obtained by image pickup means to be used for analyzing a texture of the subject's skin, wherein:

said transmitting means transmits the texture image data to said server, said receiving means receives the evaluation information including evaluation results about texture condition based on the texture image data from said server; and said display control means displays the evaluation information on said display means.

4. The system according to claim 1, further comprising dark spot image data generating means for generating B channel image data obtained by extracting B channel alone from an enlarged color image of the subject's skin surface obtained by image pickup means to be used for analyzing any dark spot on the subject's skin, wherein:

said transmitting means transmits the B channel image data to said server, said receiving means receives the evaluation information including evaluation results obtained by evaluating dark spot in the B channel image data from said server; and said display control means displays the evaluation information on said display means.

5. The system according to claim 3, wherein said display control means displays skin analysis results of the subject obtained on the basis of the evaluation information and skin analysis results obtained from persons of a same generation as the subject on the display means so that the subject's skin analysis can be compared with the skin analysis results from persons of the same generation.

6. The system according to claim 5, wherein the persons of the same generation have an age equal to the subject's age or 1 or 2 years older or younger than the subject's age on said display means.

7. The system according to claim 5, wherein said display control means displays the analysis results of the subject relative to analysis results of the persons of the same generation of the subject.

* * * * *

UNITED STATES PATENT AND TRADEMARK OFFICE
CERTIFICATE OF CORRECTION

PATENT NO.        : 7,421,105 B2                                Page 1 of 2
APPLICATION NO.   : 10/848233
DATED             : September 2, 2008
INVENTOR(S)       : Hirai et al.

It is certified that error appears in the above-identified patent and that said Letters Patent is hereby corrected as shown below:

On the title page:

Page 1, Column 2, Line 14, Other Publications, "of scales romvoed" should be changed to
--of scales removed--

Page 2, Column 2, Line 19, Other Publications, "London, GB, p. 002" should be changed to
--London, GB, Class B04, p. 002--

Column 1, Below title, add --RELATED APPLICATION DATA--

Column 2, Line 36, "(keratinized layer)" should be changed to --(keratinized layer),--

Column 6, Line 40, "skin biorhythm";" should be changed to --skin biorhythm".--

Column 6, Line 42, "DETAIL DESCRIPTION" should be changed to
--DETAILED DESCRIPTION--

Column 6, Lines 44-45, "in more detail," should be changed to --in more detail.--

Column 9, Line 21, "X not clear." should be changed to --X = not clear.--

Column 9, Line 62, "X not clear." should be changed to --X = not clear.--

Column 14, Line 67, "and (complatenes)," should be changed to --and (completeness),--

Column 15, Line 37, "customer can be," should be changed to --customer can be--

Column 18, Line 24, "(zone) maybe" should be changed to --(zone) may be--

Signed and Sealed this
Twenty-fourth Day of May, 2011

David J. Kappos
*Director of the United States Patent and Trademark Office*

Column 18, Line 28, "averaged at a may" should be changed to --average data may--

Column 20, Line 18, "in the flowchart" should be changed to --in the flow chart--

Column 21, Line 18, "(X 30 and X150)" should be changed to --(X30 and X150)--

Column 21, Lines 47-48, "on skin care" should be changed to --on skincare--

Column 22, Line 60, "250°C.," should be changed to --25°C.,--